United States Patent
Allen et al.

(10) Patent No.: US 8,410,334 B2
(45) Date of Patent: Apr. 2, 2013

(54) INVERTEBRATE MICRORNAS

(75) Inventors: Edwards Allen, O'Fallon, MO (US);
William P. Donovan, Manchester, MO (US); Gregory R. Heck, Crystal Lake Park, MO (US); James K. Roberts, Chesterfield, MO (US); Virginia Ursin, Pawcatuck, CT (US); Yuanji Zhang, Weldon Spring, MO (US)

(73) Assignee: Monsanto Technology LLC, St. Louis, MO (US)

( * ) Notice: Subject to any disclaimer, the term of this patent is extended or adjusted under 35 U.S.C. 154(b) by 790 days.

(21) Appl. No.: 12/033,178

(22) Filed: Feb. 19, 2008

(65) Prior Publication Data

US 2008/0201801 A1    Aug. 21, 2008

Related U.S. Application Data

(60) Provisional application No. 60/890,705, filed on Feb. 20, 2007.

(51) Int. Cl.
*A01H 1/00* (2006.01)
*C12N 15/82* (2006.01)
*C12N 15/87* (2006.01)
*C07H 21/04* (2006.01)

(52) U.S. Cl. ........ 800/279; 800/285; 800/286; 536/24.5

(58) Field of Classification Search ........................ None
See application file for complete search history.

(56) References Cited

U.S. PATENT DOCUMENTS

| | | | |
|---|---|---|---|
| 6,057,492 A * | 5/2000 | de Haan ........................ | 800/280 |
| 6,506,559 B1 | 1/2003 | Fire et al. | |
| 7,056,704 B2 | 6/2006 | Tuschl et al. | |
| 2004/0053411 A1 | 3/2004 | Cullen et al. | |
| 2004/0268441 A1* | 12/2004 | Vance et al. .................. | 800/288 |
| 2005/0059005 A1 | 3/2005 | Tuschl et al. | |
| 2005/0144669 A1 | 6/2005 | Reinhert et al. | |
| 2006/0009402 A1 | 1/2006 | Zamore et al. | |
| 2006/0272049 A1* | 11/2006 | Waterhouse et al. ......... | 800/279 |

OTHER PUBLICATIONS

Timmons and Fire (1998) "Specific interference by ingested dsRNA" Nature, 395:854.
Zeng et al. (2002) "Both Natural and Designed Micro RNAs Can Inhibit the Expression of Cognate . . . " Mol. Cell, 9:1327-1333.
Lee and Ambros (2001) "An Extensive Class of Small RNAs in *Caenorhabditis elegans*" Science, 294:862-864.
Du et al. (2005) "microPrimer: the biogenesis and function of micro RNA" Development, 132:4645-4652.
Lim et al. (2003) "The microRNAs of *Caenorhabditis elegans*" Genes Dev., 17:991-1008.
Bartel et al. (2004) "MicroRNAs: Genomics, Biogenesis, Mechanism, and Function" Cell, 116:281-297.
Huang et al. (2006) "Engineering broad root-knot resistance in transgenic plants" Proc. Natl. Acad. Sci. U.S.A., 103:14302-14306.
Montgomery et al. (1998) "RNA as a target of double-stranded RNA-mediated . . . " Proc. Natl. Acad. Sci. U.S.A., 95:15502-15507.
Ruby et al. (2007) "Evolution, biogenesis, expressin, and target predictions of a substantially expanded set . . . " Genome Res., 17:1850-1864.
Paddison et al (2002) "Short hairpin RNAs (shRNAs) induce sequence-specific silencing" Genes Dev., 16:948-958.
Stark et al. (2007) "Systematic discovery and chacterization of fly microRNAs . . . " Genome Res., 17:1865-1879.
Mao et al. (2007) "Silencing a cotton bollworm P450 monooxygenase gene . . . " Nature Biotechnol., 25:1307-1313.
Baum et al. (2007) "Control of coleopteran insect pests through RNA interference" Nature Biotechnol., 25:1322-1326.
Fire et al. (1991) "Production of antisense RNA leads to effective and specific inhibition . . . " Development, 113:503-514.
Tran et al. (2006) "MicroRNA enrichment among short 'ultraconserved' sequences in insects" Nucl. Acids Res., 34:1-10.
Caplen et al. (2001) "Specific inhibition of gene expression . . . " Proc. Natl. Acad. Sci. U.S.A., 98:9742-9747.
Extended European Search Report, for EP Application No. 08743490.8, mailed Jul. 2, 2010.
Jan. 31, 2011 Reply to EPO Communication for European Patent Application 08743490.8.
Office Action issued in EP 087434908 on Apr. 18, 2012.
Patent Examination Report No. 1 issued in AU 2008218813 on Aug. 15, 2012.
2nd Office Action issued in CN 2008800104709 on Jul. 18, 2012.

* cited by examiner

*Primary Examiner* — Li Zheng
(74) *Attorney, Agent, or Firm* — Maria Margarita D. Unson; Timothy K. Ball, Esq.; Thomas E. Kelley, Esq.

(57) ABSTRACT

This invention provides a non-natural transgenic plant cell expressing at least one invertebrate miRNA in planta for suppression of a target gene of an invertebrate pest or of a symbiont associated with the invertebrate pest, recombinant DNA constructs for expression of at least one invertebrate miRNA in planta and methods of use thereof, a non-natural transgenic plant containing the non-natural transgenic plant cell of this invention, a non-natural transgenic plant grown from the non-natural transgenic plant cell of this invention, and non-natural transgenic seed produced by the non-natural transgenic plants, as well as commodity products produced from a non-natural transgenic plant cell, plant, or seed of this invention.

21 Claims, 12 Drawing Sheets

FIGURE 1

AAAATTTTCACTAAGGTCGTCGCGATCCGGGACGCGAATTCGCGGAACAGCCCCGACC
CTTTCAGGTAACAACGCCCGCCACCCACAGGTAGGTGTTTATAGGACAAGAAAGTGGG
TATAAAAGATCTAGCCGCTGGCAAGGAAGTCATCAGTTACCAACGCATCTTCAAAGTGT
AAGGATCCCGCAGTGAGAAGCGAAGTCTTAAAGTTTGGAATAGCAATTATACGACAAA
CCTTGTTCGGTTTTGCCAATTTCCAAGCCAGCACTGGGTAAAGTTTGTCCTATAATCCC
GAAACGACGACCAGCTAATTGTGAGCCACCTAAGGTCCCGATCCTGGGATGCATCTTG
TGCAGTTATGTTTCAATCTCACATCACTGGGCAAAGTGTGTCTCAAGATCCTGGCCAC
ATCGTCGCAACTTCAAATCAATTAAATCAAAAAATCAAGAGTAAGTGATATTGGGCACTC
CAGTTTTAAAATTGAATGGCGAATGTCGGTATGGTCTCTTTTTCAAAGAAAGGTTTCGA
TTAAGCGAAGTGACTAGACCGAACACTCGTGCTATAATTTTAAAATATTCAACATGCTC
AGTAAAGTTGCGAGTGAAAATTAAAATATTATGGAGCGGTTGCAATTAGTTTCTTTGGTC
GTCCAGCCTTAGGTGATTTTTCCGGTCATAAAGCTAGACAACCATTGAAGTTCGTTGT
GGCATTAGCAGCACCACGAGTCAAGAAATTATGTTAAGTGATCCCCAAATTCATCGGGC
CATTCGCTAAAAGGAACGATCGTTGTGATATGAGTTGTTTCCTAACATATCACAGTGA
TTTTCCTTTATAACGCATGTTTAAAGTCCACAACTCATCAAGGAAAATGAAAGTCAAAGT
TGGCAGCTTACTTAAACTTAATCACAGCCTTTAATGTAGAGGGAATAGTTGCTGTGCTG
TAAGTTAATATACCATATCTATATCACAGTGGCTGTTCTTTTTGTACCTAAAGTGCCTA
ACATCATTATTTAATTTTTTTTTTTTTGGCACACGAATAACCATGCCGTTTTTAACCCAA
GGGAACTTCTGCTGCTGATATATTATTGAAAAACTACTATATCACAGTGGCTGTTCTTT
TTGGTTGCACGGCCAATTCCAACGATTTGTCATTTGTGGCACGCATTTGTGTCACCTCA
GTGCGAAAATTGAAAATTGTACAAAAAGAAGGGAACGGTTGCTGATGATGTAGTTTGA
AACTCTCACAATTTATATCACAGTGGCTGTTCTTTTTTGTTTGGCAATCGATCTACGTTC
AGTGGTTTGCCAGGACATGAAACAGAAATATTTTCCGTCAACAGACTTCTGATTGCACA
AATTCCTCAAGCTTTGAACATTTGGGAAAAACTGATGAGACGTTGGTTTTCTAGCTTGTG
CATCAATTCGTCATTTGTCTGCAGTTTTGTCAATCTTTAATTGCACTTTACAATTCATTGC
TTTTTGTTCAATCATTTTTGGGTGGT (SEQ ID NO. 1)

FIGURE 2

```
            c       c   uu    u   c aau
     auuaua gacaaac uug  cggu uug c    u
     ||||||| ||||||| |||  |||| ||| |    u          dme-mir-309  (SEQ ID NO. 11)
     uaauAU CUGUUUG AAU  GUCA Gac g    c
            C       A    GG   C   c aac c        uc    g    u    uuc
     gauc uggaugca uugu cagu augu   a
     |||| |||||||| |||| |||| ||||   a                dme-mir-3  (SEQ ID NO. 12)
     cuag ACUCUGUGU AACG GUCA Uaca   u
          a         GA   G    C    cuc ---         aaug    a  -   a       ucuuuuucaaagaaag
   uuaaaauug    gcga ugu cggu uggu c                         g
   |||||||||    |||| ||| |||| ||||                             dme-mir-286  (SEQ ID NO. 13)
   aauuuuaau    UGCU ACA GCCA AUCAG                          u
 uaa          aUCG   C   A    G       ugaagcgaauuagcuu ug    u gu   uu     c   c   cuuag        u
     u   caau a  uuc  uggu guc agc      gugauu u
     |   |||| |  |||  |||| ||| |||      |||||| u      dme-mir-4  (SEQ ID NO. 14)
     g   guug u  aAG  ACCA CAG UCG      UAcugg c
       gu    c ug    UU    A   A   --AAA       c ---gcua    c                     aguug
        AAAGGAA GAUCGUUGUGAUAUG            u
        ||||||| ||||||||||||||||            u         dme-mir-5  (SEQ ID NO. 15)
        uuuccuu uuagugacacuauac            u
     cgcaaua    -                    aaucc -uuuaaug          ug     c    ag uaau
     uagagggaauagu  cugug ugua  u       a
     |||||||||||||  ||||| ||||  |       u             dme-mir-6-1 (SEQ ID NO. 16)
     gUUUUUCUUGUCG  GACAC AUau  a       a
     aaauccau          GU    U     cu uacc c      uu ug   c           u  -  g
     uaacc aagggaac  c  cug ugauaua ua uu a
     ||||| ||||||||  |  ||| ||||||| || ||                dme-mir-6-2 (SEQ ID NO. 17)
     guugg UUUUCUUG  G  GAC ACUAUau au aa a
         u      UC GU   -           c  c  a a          ug   a         u   aaa
     caaa agaagggaacggu  cug ugauuag uug   c
     |||| ||||||||||||  |||  ||||||| |||   u             dme-mir-6-3 (SEQ ID NO. 18)
     guuu uUUUUUCUUGUCG GAC ACUAUauu aac   c
         g           GU   -         u   acu
```

FIGURE 5 mature miRNA SEQ ID NO. 53 embedded in pre-miRNA SEQ ID NO. 57 (from locus HG3_LIB5513-477-A1-M1-H4)

mature miRNA SEQ ID NO. 54 embedded in pre-miRNA SEQ ID NO. 58 (from locus HG3_34113.C1)

mature miRNA SEQ ID NO. 54 embedded in pre-miRNA SEQ ID NO. 59 (from locus HG3_18268.C1)

mature miRNA SEQ ID NO. 54 embedded in pre-miRNA SEQ ID NO. 60 (from locus HG3_12307.C1)

mature miRNA SEQ ID NO. 54 embedded in pre-miRNA SEQ ID NO. 61 (from locus HG3_1908.C2)

FIGURE 5 (continued)

| | |
|---|---|
| mature miRNA SEQ ID NO. 54 embedded in pre-miRNA SEQ ID NO. 62 (from locus HG3_LIB5513-708-A1-M1-E9) | (RNA hairpin structure, 305–325) |
| mature miRNA SEQ ID NO. 54 embedded in pre-miRNA SEQ ID NO. 63 (from locus HG3_LIB5513-103-A1-M1-G4) | (RNA hairpin structure, 120–141) |
| mature miRNA SEQ ID NO. 54 embedded in pre-miRNA SEQ ID NO. 64 (from locus HG3_LIB5519-507-A1-M1-F3) | (RNA hairpin structure, 347–368) |
| mature miRNA SEQ ID NO. 55 embedded in pre-miRNA SEQ ID NO. 65 (from locus HG3_1898.C5) | (RNA hairpin structure, 711–687) |
| mature miRNA SEQ ID NO. 56 embedded in pre-miRNA SEQ ID NO. 66 (from locus HG3_25240.C1) | (RNA hairpin structure, 1168–1190) |

FIGURE 5 (continued)

FIGURE 6
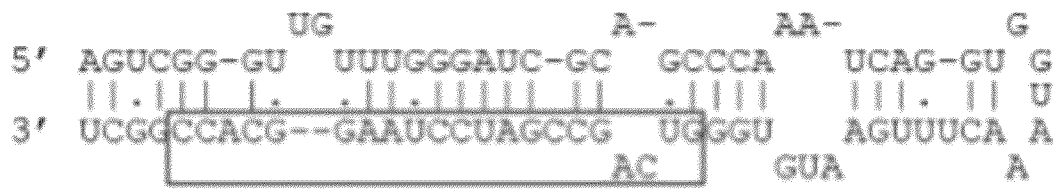
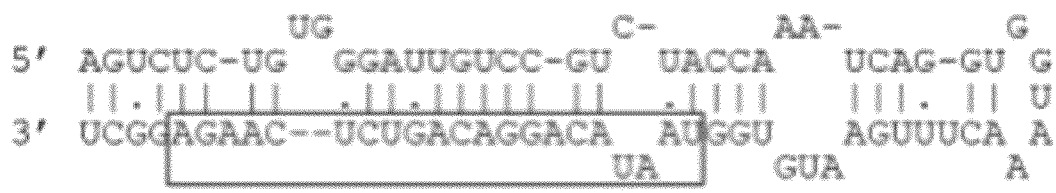
A
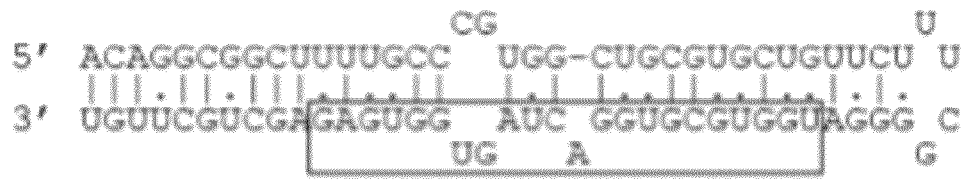
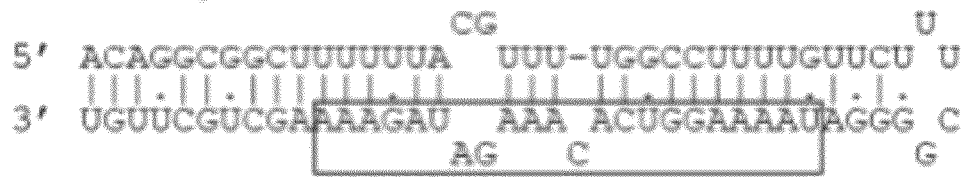
B

FIGURE 7
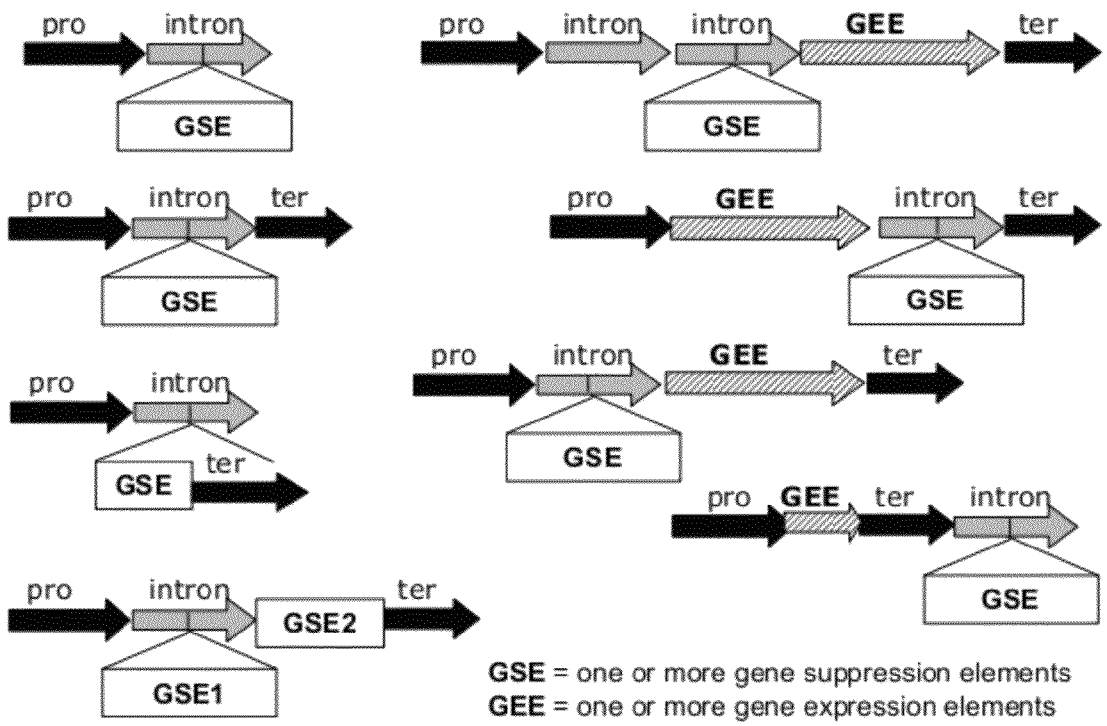
A
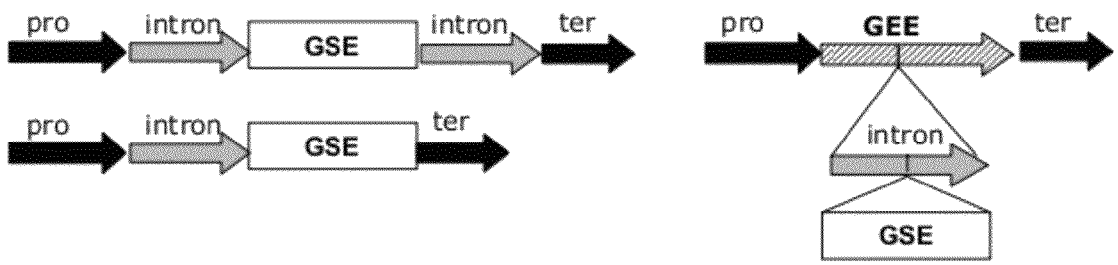
B

US 8,410,334 B2

INVERTEBRATE MICRORNAS

CROSS-REFERENCE TO RELATED APPLICATIONS AND INCORPORATION OF SEQUENCE LISTINGS

This application claims the benefit of priority of U.S. Provisional Patent Application 60/890,705, filed 20 Feb. 2007, which is incorporated by reference in its entirety herein. The sequence listing contained in the file named "38-21_54478_A.txt", which is 35 kilobytes (measured in operating system MS-Windows) and was created on 15 Feb. 2007 and filed with U.S. Provisional Patent Application 60/890,705 on 20 Feb. 2007, is incorporated herein by reference.

INCORPORATION OF SEQUENCE LISTING

The sequence listing that is contained in the file named "38-21_54478_B.txt", which is 35 kilobytes (measured in operating system MS-Windows), created on 12 Feb. 2008, is filed herewith and incorporated herein by reference.

FIELD OF THE INVENTION

This invention relates to novel microRNAs and microRNA precursors identified from invertebrates, as well as recombinant DNA constructs including such novel miRNAs, miRNA precursors, and miRNA recognition sites corresponding to the miRNAs. Also disclosed are non-natural transgenic plant cells, plants, and seeds containing in their genome a recombinant DNA construct of this invention. Further provided are methods of gene suppression using recombinant DNA constructs of this invention.

BACKGROUND OF THE INVENTION

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available on line at microma.sanger.ac.uk/sequences; also see Griffiths-Jones et al. (2003) Nucleic Acids Res., 31:439-441). MicroRNAs were first reported from nematodes and have since been identified in other invertebrates; see, for example, Lee and Ambros (2001) Science, 294:862-864; Lim et al. (2003) Genes Dev., 17:991-1008; Stark et al. (2007) Genome Res., 17:1865-1879. MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) Nature Rev. Mol Cell Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell Biol., 6:376-385.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length, whereas in animals 22 nucleotide long miRNAs are most commonly found. For a recent review of miRNA biogenesis in both plants and animals, see Kim (2005) Nature Rev. Mol. Cell Biol., 6:376-385. Additional reviews on miRNA biogenesis and function are found, for example, in Bartel (2004) Cell, 116:281-297; Murchison and Hannon (2004) Curr. Opin. Cell Biol., 16:223-229; and Dugas and Bartel (2004) Curr. Opin. Plant Biol., 7:512-520. Furthermore, although one recent report describes a miRNA (miR854) from Arabidopsis that also is found in animals (Arteaga-Vazquez et al. (2006) Plant Cell, 18:3355-3369), miRNA conservation generally appears to be kingdom-specific. Animal miRNAs have many characteristic dissimilar to their plant counterparts, including shorter miRNA precursor fold-backs (about 90 nucleotides in animals versus about 180 nucleotides in plants) with the mature miRNA sequence tending to be found at the base of the stem, a higher number of mismatches within the foldback, and deriviation from from polycistronic messages. Whereas animal miRNAs generally anneal imperfectly to the 3' untranslated region (UTR) of their target mRNA, most plant miRNAs are characterized by having perfect or near-perfect complementarity to their target sequence, which is usually in the coding region, with only a few examples of miRNAs having binding sites within the UTRs of the target mRNA; see Rhoades et al. (2002) Cell, 110:513-520; Jones-Rhoades et al. (2006) Annu. Rev. Plant Biol., 57:19-53. These significant differences between plant and animal miRNAs make it generally unlikely that miRNAs will be processed and function across kingdoms.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2)

the expression of an engineered (non-native) miRNA or miRNA precursor sequence to suppress a target gene; (3) expression of a transgene with a miRNA recognition site, wherein the transgene is suppressed when the mature miRNA is expressed; (4) expression of a transgene driven by a miRNA promoter.

Animal miRNAs have been utilized as precursors to express specific miRNAs in animal cells; for example, the human miR-30 precursor was expressed as the native sequence and as a modified (artificial or engineered) miRNA in cultured cells (Zeng et al. (2002) *Mol. Cell*, 9:1327-1333, and Zeng et al. (2005) *J. Biol. Chem.*, 280:27595-27603). A single mature miRNA is precisely processed from a given precursor, and therefore such "artificial" or engineered miRNAs offer an advantage over double-stranded RNA (dsRNA) in that only a specific miRNA sequence is expressed, limiting potential off-target effects. Although animal miRNAs typically interact with imperfect target sequences in the 3' UTR, synthetic miRNAs with perfect target complementarity also can guide target cleavage (see Zeng et al. (2003) *RNA*, 9:112-123 and Zeng et al (2003) *Proc. Natl. Acad. Sci. U.S.A.*, 100:9779-9784).

Small RNAs, referred to as short interfering RNAs (siRNAs) and micro RNAs (miRNAs), have been shown to regulate gene expression in plants and animals (Valencia-Sanchez et al. (2006) *Genes Dev.*, 20:515-524; Nelson et al. (2003) *Trends Biochem. Sci.*, 28:534-540). Experimental alteration of siRNA levels result in phenotypic effects in nematodes (Timmons and Fire (1998) *Nature*, 395:8543). A plant that transgenically expressed siRNA complementary to the root-knot nematode 16D10 gene was shown to have resistance to four species of root-knot nematodes (Huang et al. (2006) *Proc. Natl. Acad. Sci. U.S.A.*, 103:14302-14306). This invention discloses the use of recombinant invertebrate miRNAs expressed in planta to similarly regulate expression in an invertebrate that ingests the miRNAs.

This invention discloses recombinant DNA constructs encoding invertebrate mature miRNAs and their miRNA precursors, which are designed to be expressed in planta. In some embodiments, the invertebrate miRNA precursors are engineered to express artificial miRNAs designed to suppress or silence specific invertebrate genes and thereby confer upon a plant expressing the miRNAs resistance to an invertebrate that ingests the miRNAs. In many cases, RNAi (siRNA or miRNA) transcripts that are intended to suppress an invertebrate target are preferably ingested by the invertebrate as larger transcripts, that is, larger than the 21 to 24 nucleotide fragments typically resulting from in planta processing. Thus, RNAi transcripts intended for ingestion are preferably designed to be resistant to in planta processing. The recombinant invertebrate miRNAs of this invention are preferably resistant to the plant-specific endogenous miRNA processing (in comparison to plant-derived miRNAs), but are preferably readily recognized in invertebrate cells where they are processed to the mature miRNA.

SUMMARY OF THE INVENTION

In one aspect, this invention provides a non-natural plant having resistance to an invertebrate pest that ingests RNA from the plant, wherein the plant includes a transgenic plant cell having in its genome a recombinant DNA construct that is transcribed in the transgenic plant cell to a recombinant miRNA precursor; and the recombinant miRNA precursor includes a single strand of RNA that folds into the secondary structure of an invertebrate miRNA precursor and that includes at least one stem-loop that is processed to a mature miRNA; and the mature miRNA suppresses expression of at least one target gene of the invertebrate pest (or of a symbiont that is associated with the invertebrate pest), thereby conferring on the non-natural plant resistance to the invertebrate pest.

Another aspect of this invention provides the recombinant DNA construct that is transcribed in the non-natural transgenic plant cell to a recombinant miRNA precursor. In many embodiments, the recombinant DNA construct further includes one or more elements selected from: (a) a promoter functional in a plant cell; (b) a transgene transcription unit; (c) a gene suppression element; and (d) a transcription regulatory/transcript stabilizing element.

In a further aspect, this invention provides a non-natural transgenic plant cell having in its genome recombinant DNA that is transcribed in the non-natural transgenic plant cell to a recombinant miRNA precursor, wherein the recombinant miRNA precursor includes a single strand of RNA that folds into the secondary structure of an invertebrate miRNA precursor and that includes at least one stem-loop that is processed to a mature miRNA, and wherein the mature miRNA suppresses expression of at least one target gene of an invertebrate (or of a symbiont that is associated with the invertebrate pest). Also provided are a non-natural transgenic plant containing the transgenic plant cell of this invention, a non-natural transgenic plant grown from the transgenic plant cell of this invention, and non-natural transgenic seed produced by the transgenic plants, as well as commodity products produced from a non-natural transgenic plant cell, plant, or seed of this invention.

Other specific embodiments of the invention are disclosed in the following detailed description.

BRIEF DESCRIPTION OF THE DRAWINGS

FIG. 1 depicts a non-limiting example of multiple invertebrate miRNA precursors, a *Drosophila melanogaster* "8-miR" sequence (SEQ ID NO. 1), as described in Example 1. The individual miRNA precursors indicated by bold underlined text.

FIG. 2 depicts the fold-back structure (that is, the secondary structure of the miRNA precursor including a stem-loop that is processed to the mature miRNA) for each of the 8 miRNA precursors of the *Drosophila melanogaster* "8-miR" sequence described in Example 1 and Table 1. The mature miRNA is indicated within the fold-back structure in bold capitals. The stem region of the fold-back structure is generally indicated by the vertical hatch marks indicating base pairing between the first and second segments of the folded strand; the loop region is depicted in each case to the right of the stem region. This illustrates non-limiting embodiments of mismatches (see paragraph 0024), wherein at least one nucleotide of the first segment is unpaired within the partially double stranded RNA formed by hybridization of the first and second segments that are included in the stem region. One example of a mismatch is the at least one extra or at least one missing nucleotide on the second segment at the position corresponding to the nucleotide in question of the first segment in dme-mir-5 (SEQ ID NO. 15). Another example of a mismatch is illustrated by the multiple non-base-paired nucleotides in dme-mir-309 (SEQ ID NO. 11).

FIG. 5 depicts non-limiting examples of fold-back structures (i.e., secondary structures of invertebrate miRNA precursors listed in Table 4, each including at least one stem-loop that is processed to a mature miRNA, wherein the stem-loop includes a stem region and a loop region), as described in Example 2.

FIG. 6A depicts a native "SCN15" pre-miRNA sequence (SEQ ID NO. 57) of which the complementary region of the foldback was changed to maintain the original paired and unpaired bases, yielding the corresponding engineered pre-miRNA sequence "SCN15-MIRMSP1" (SEQ ID NO. 92), as described in Example 4. FIG. 6B depicts a native "SCN25" pre-miRNA sequence (SEQ ID NO. 58) of which the complementary region of the foldback was changed to maintain the original paired and unpaired bases, yielding the corresponding engineered pre-miRNA sequence "SCN25-MIRcgh1" (SEQ ID NO. 96), as described in Example 5.

FIG. 7 schematically depicts non-limiting recombinant DNA constructs as described in Example 6. For use in *Agrobacterium*-mediated transformation of plant cells, at least one T-DNA border is generally included in each construct (not shown). These constructs include a promoter element ("pro"), an intron flanked on one or on both sides by non-protein-coding DNA, an optional terminator element ("ter"), at least one first gene suppression element ("GSE" or "GSE1") for suppressing at least one first target gene, and can optionally include at least one second gene suppression element ("GSE2") for suppressing at least one second target gene, at least one gene expression element ("GEE") for expressing at least one gene of interest, or both. In embodiments containing a gene expression element, the gene expression element can be located adjacent to (outside of) the intron. In one variation of this embodiment (not shown), the gene suppression element (embedded in an intron flanked on one or on both sides by non-protein-coding DNA) is located 3' to the terminator. In other constructs of the invention (not shown), a gene suppression element (not intron-embedded) is located 3' to the terminator.

DETAILED DESCRIPTION OF THE INVENTION

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

Plant Having Resistance to an Invertebrate Pest

In one aspect, this invention provides a non-natural plant having resistance to an invertebrate pest that ingests RNA from the plant, wherein the plant includes a transgenic plant cell having in its genome a recombinant DNA construct that is transcribed in the transgenic plant cell to a recombinant miRNA precursor; and the recombinant miRNA precursor includes a single strand of RNA that folds into the secondary structure of an invertebrate miRNA precursor and that includes at least one stem-loop that is processed to a mature miRNA; and the mature miRNA suppresses expression of at least one target gene of the invertebrate pest (or of a symbiont that is associated with the invertebrate pest), thereby conferring on the non-natural plant resistance to the invertebrate pest.

Figure 3:
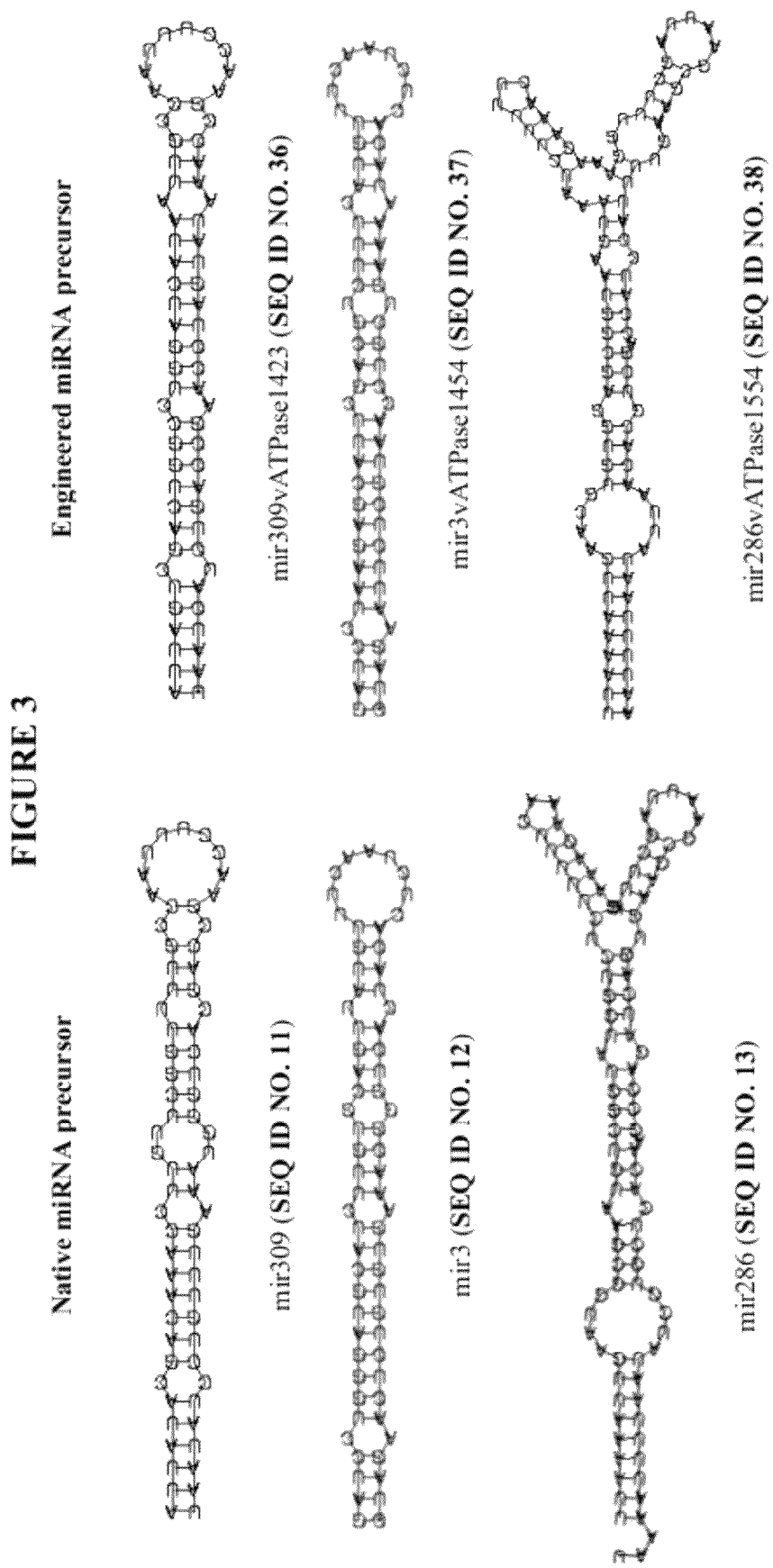
FIG. 3 depicts native miRNA precursors and for each, the corresponding engineered miRNA precursor, as listed in Table 2 and described in Example 1. Secondary structure (i.e., fold-back structure) in the engineered miRNA precursor is preferably maintained to be similar to that of the corresponding native miRNA precursor. Note that loop regions may include more than a single single-stranded segment (see the structures of SEQ ID NO. 13 and SEQ ID NO. 38).
Figure 3:
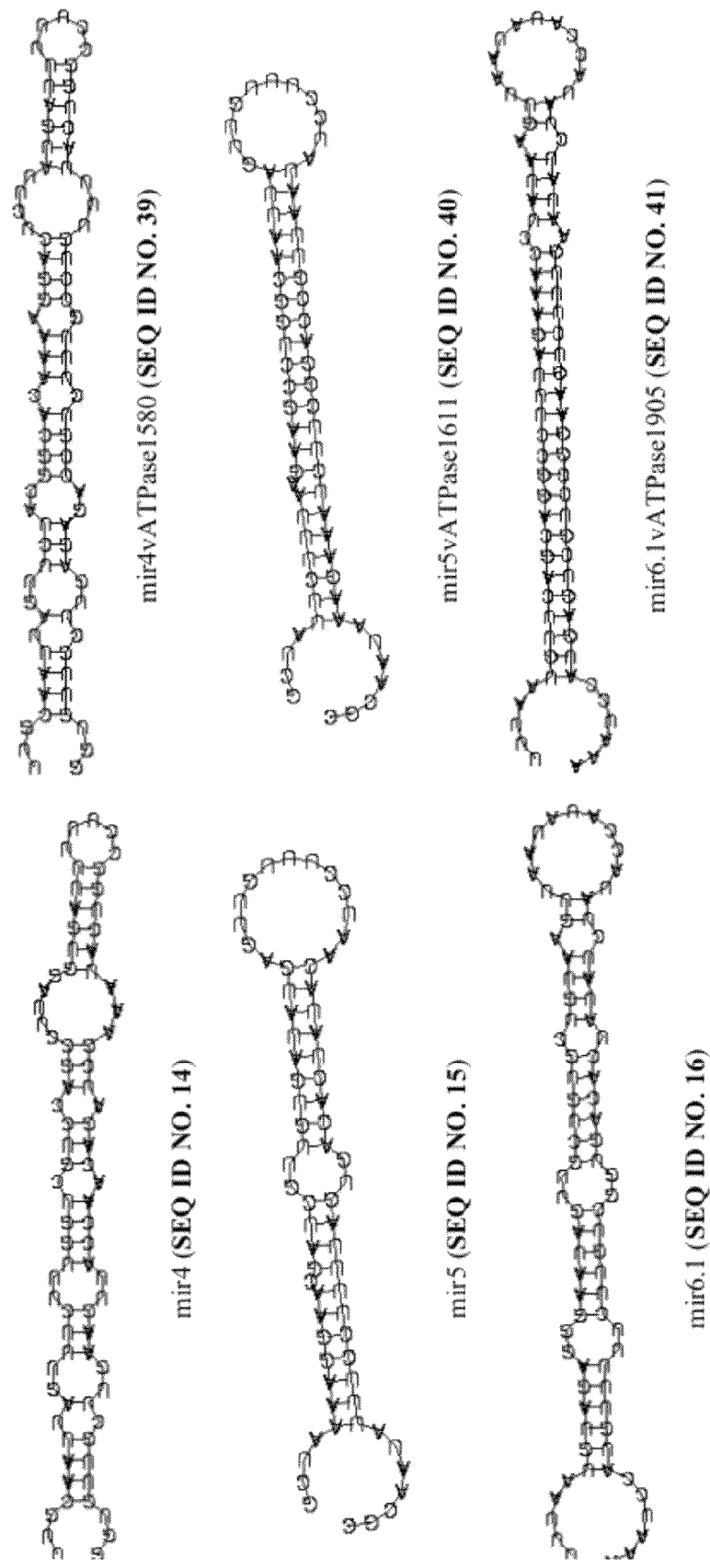
Figure 3:
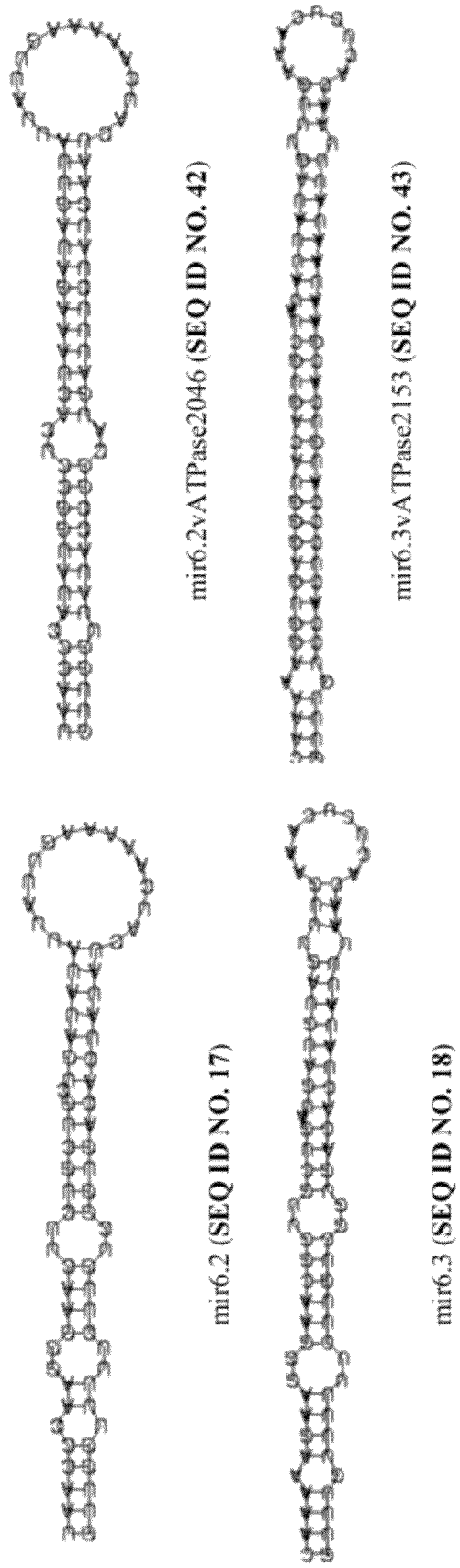
Figure 4:
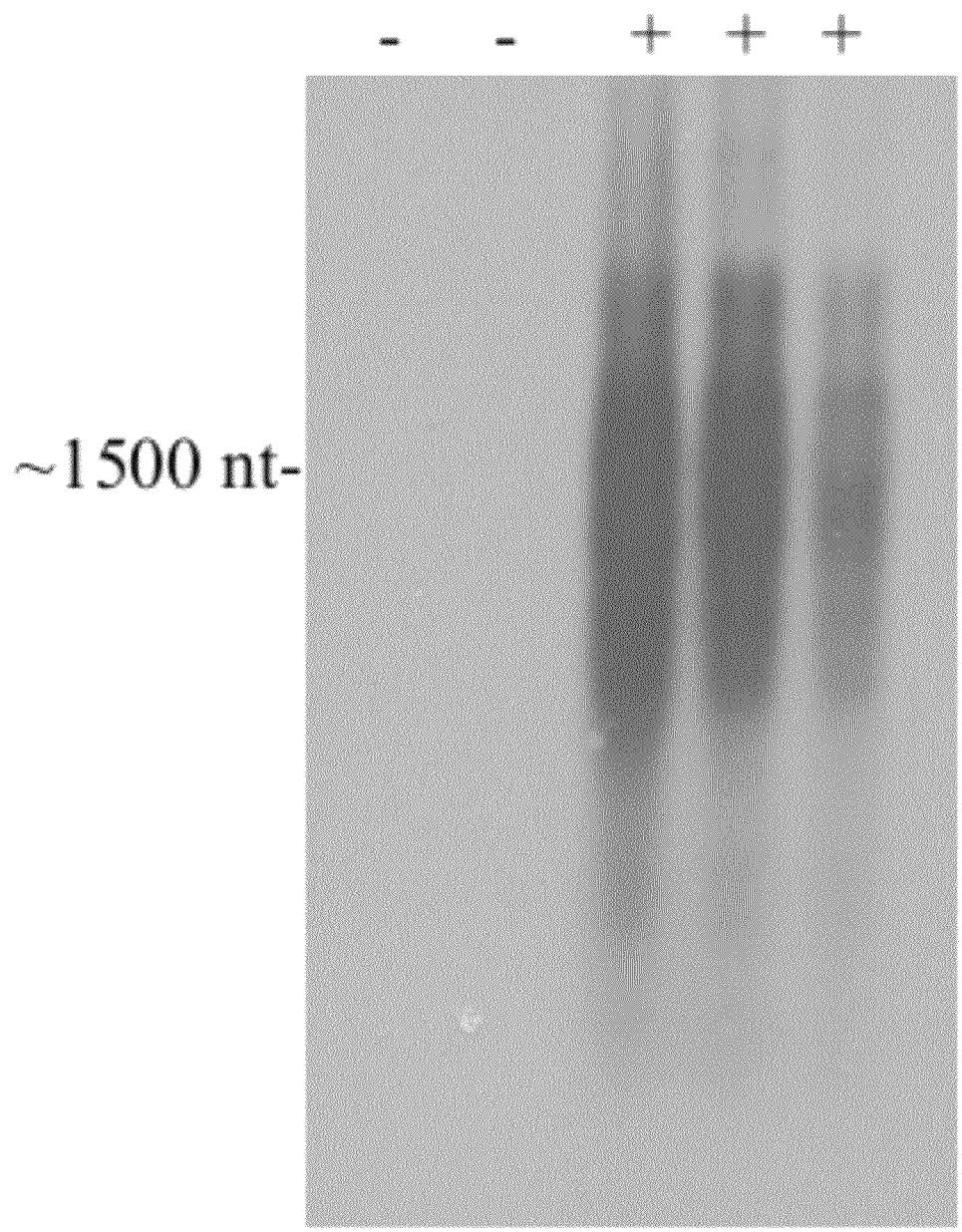
FIG. 4 depicts a Northern blot used to test in planta stability of an engineered miRNA precursor, as described in Example 1. "+" indicates RNA from plants transformed with pMON97878; "−" indicates negative controls. "8mirvATPase-16" (SEQ ID NO. 46) RNA was present in tobacco plants as both full-length "8mirvATPase-16" transcript and as degraded RNA, demonstrating that "8mirvATPase-16" RNA is more stable in plants than is the corresponding double-stranded RNA produced from an inverted repeat (i.e., sense adjacent to anti-sense of the same target gene), which was found to be entirely cleaved to small RNAs in planta (data not shown).

In another aspect, the recombinant DNA construct that is transcribed in the transgenic plant cell to a recombinant miRNA precursor is also specifically disclosed and claimed herein. The recombinant DNA construct is made by techniques known in the art, such as those described under the heading "Making and Using Recombinant DNA Constructs" and illustrated in the working Examples. The recombinant DNA construct is particularly useful for making transgenic plant cells, transgenic plants, and transgenic seeds as discussed below under "Making and Using Transgenic Plant Cells and Transgenic Plants". The recombinant miRNA precursor is generally transcribed as a single strand of RNA. This single strand of RNA includes at least one stem-loop that can be regarded as equivalent to a naturally occurring pre-miRNA, in that it is processed to a mature miRNA. The stem-loop is formed when the single strand folds back on itself and sufficient base pairing occurs to stabilize the resulting folded structure. The stem-loop includes a stem region and a loop region, all within the same single strand of RNA. The stem region includes a first segment and a second segment, which are joined through the loop region. Note that the loop region can include structures more complex than a simple single-stranded loop, a non-limiting example of which is illustrated by mir286 (SEQ ID NO. 13) and its engineered counterpart (SEQ ID NO. 38) in FIG. 3. The first segment includes at least 19 contiguous nucleotides for silencing a messenger RNA encoding the target gene. The second segment contains at least 19 contiguous nucleotides. The first segment and second segment are generally of similar length (in terms of number of contiguous nucleotides making up each segment) but are not necessarily of identical length. The loop region is located on the single strand between the first and second segments. The first and second segments hybridize to form partially double stranded RNA, wherein at least one nucleotide of the first segment is unpaired; that is, within the partially double stranded RNA, there is at least one nucleotide of the first segment that is mismatched to the corresponding position on the second segment. The mismatch results in a bulge or loop or kink in the otherwise substantially double-stranded stem region. The mismatch can be due to, for example, at least one nucleotide of the second segment that does not base-pair to the nucleotide in question of the first segment, or at least one extra or at least one missing nucleotide on the second segment at the position corresponding to the nucleotide in question of the first segment. FIG. 2 illustrates non-limiting examples of mismatches.

The first segment of the stem region includes at least 19 contiguous nucleotides for silencing a messenger RNA encoding the target gene (the "target mRNA"); the mature miRNA that is processed from the stem-loop includes these at least 19 contiguous nucleotides. These at least 19 contiguous nucleotides have at least about 70% complementarity to a segment of equivalent length (that is, at least about 70% complementarity to a segment having about the same number of contiguous nucleotides) in the target mRNA. For example, where the first segment of the stem region consists of exactly 19 contiguous nucleotides for silencing the target mRNA, these 19 contiguous nucleotides can include 13 nucleotides (13/19=68% complementarity), 14 nucleotides (14/19=74% complementarity), 15 nucleotides (15/19=79% complementarity), 16 nucleotides (16/19=84% complementarity), 17 nucleotides (17/19=89% complementarity), 18 nucleotides (18/19=95% complementarity), or even 19 nucleotides (19/19=100% complementarity) that are complementary to a 19-nucleotide segment in the target mRNA.

In preferred embodiments, the at least 19 contiguous nucleotides have at least about 75%, or at least about 80%, or at least about 85%, or at least about 90% complementarity to a segment of equivalent length in the target mRNA. In one particularly preferred embodiment, the at least 19 contiguous nucleotides have at least about 95% complementarity to a segment of equivalent length in the target mRNA. In another particularly preferred embodiment, the at least 19 contiguous nucleotides have 100% complementarity to a segment of equivalent length in the target mRNA.

The degree of complementarity between the stem region's first segment's at least 19 contiguous nucleotides to a segment of equivalent length in the target mRNA is readily selected by one of skill in the art. It has been reported that base pairing between nucleotides located towards the 5' end of the mature miRNA to the target mRNA is comparatively important in the ability of a mature miRNA to silence expression of the target mRNA (see, for example, Doensch and Sharp (2004) *Genes Dev.*, 18:504-511), and it is expected that high complementarity between the 5' end of the mature miRNA to the target can allow a relatively higher degree of mismatch between nucleotides closer to the 3' end of the mature miRNA and the target (and vice versa). Thus, in a preferred embodiment, the nucleotide sequence of the stem region's first segment's at least 19 contiguous nucleotides is selected so that the mature miRNA processed from the stem-loop is perfectly complementary to the target mRNA at the 5'-most 8 nucleotides of the mature miRNA. In another preferred embodiment, the nucleotide sequence of the stem region's first segment's at least 19 contiguous nucleotides is selected so that the mature miRNA processed from the stem-loop is perfectly complementary to the target mRNA at nucleotide positions 2, 3, 4, 5, 6, and 7 (from the 5' end) of the mature miRNA. In another preferred embodiment, the nucleotide sequence of the stem region's first segment's at least 19 contiguous nucleotides is designed so that the mature miRNA processed from the stem-loop structure has few or no G:U wobble base pairs.

The loop region of the stem-loop typically includes between about 4 to about 40 nucleotides. In some preferred embodiments, the loop region includes consecutive nucleotides of a native loop sequence of the invertebrate miRNA precursor. In some embodiments, the loop region is identical to a native loop sequence of the invertebrate miRNA precursor.

In some embodiments, the stem-loop is processed to a mature miRNA, typically of 21, 22, 23, 24, 25, or 26 nucleotides in length, in the transgenic plant cell. In other embodiments, the stem-loop preferably remains relatively intact (that is, substantially uncleaved to smaller polynucleotides) in the transgenic plant cell, but is processed to a mature miRNA (typically of 21, 22, 23, 24, 25, or 26 nucleotides in length) in the gut or in or on a cell of an invertebrate that ingests RNA from the plant that includes the transgenic plant cell.

In one embodiment, the single strand of RNA includes a single stem-loop that is processed to a mature miRNA. In other embodiments, the single strand of RNA includes multiple stem-loops that are processed to mature miRNAs. Where multiple stem-loops are present, they can consist of multiples of the same stem-loop, or multiple different stem-loops. In one preferred embodiment, the single strand of RNA includes multiple stem-loops that correspond to a group of invertebrate miRNAs that are natively transcribed in a single polycistronic transcription unit. One non-limiting example is a single strand of RNA including multiple stem-loops that correspond to a polycistronic group of 8 miRNAs found on Chromosome 2R in *Drosophila melanogaster* (SEQ ID NO. 1, see Example 1).

The target gene of the invertebrate pest (or of a symbiont that is associated with the invertebrate pest) that is suppressed by the mature miRNA can be a single target gene, or can be multiple target genes (e.g., multiple alleles of a given target gene, or multiple unrelated target genes). Target genes of interest are described in detail in the section "Target Genes and Pest Invertebrates".

In some embodiments, the at least one target gene is an endogenous or native target of an invertebrate miRNA natively expressed from the invertebrate miRNA precursor. In these embodiments, the mature miRNA processed from the stem-loop is identical (or nearly identical) to the mature miRNA natively processed from the naturally occurring invertebrate miRNA precursor. Generally, therefore, the recombinant miRNA precursor is substantially similar to the invertebrate miRNA precursor, although the recombinant miRNA precursor is designed to express the mature miRNA generally under non-native conditions. In a non-limiting example, the recombinant DNA encodes a native invertebrate miRNA precursor, expressed under the control of a promoter that differs from the native promoter of the invertebrate miRNA precursor.

In other embodiments, the at least one target gene is other than an endogenous target of an invertebrate miRNA natively expressed from the invertebrate miRNA precursor. In these embodiments, the mature miRNA processed from the stem-loop is an "engineered miRNA", that is, a mature miRNA having an artificial sequence designed to suppress a target gene of choice. Factors considered in the design of such an engineered miRNA sequence are described in detail in the section "Target Genes and Pest Invertebrates", in the working examples, and elsewhere in this disclosure.

The invertebrate pest is at least one or more invertebrate selected from the group consisting of insects, arachnids (e.g., mites), nematodes, molluscs (e.g., slugs and snails), and annelids, and can include an invertebrate associated with an invertebrate pest in a symbiotic relationship (e.g., the mutualistic relationship between some ant and aphid species). The term "symbiotic" relationship as used herein encompasses both facultative (non-obligate) and obligate symbioses wherein at least one of the two or more associated species benefits, and further includes mutualistic, commensal, and parasitic relationships. Symbionts also include non-invertebrate symbionts, such as prokaryotes and eukaryotic protists. An invertebrate pest can be controlled indirectly by targetting a symbiont that is associated, internally or externally, with the invertebrate pest. For example, prokaryotic symbionts are known to occur in the gut or other tissues of many invertebrates, including invertebrate pests of interest. Non-limiting examples of a targetted symbiont associated with an invertebrate pest include the aphid endosymbiotic bacteria *Buchnera*; *Wolbachia* bacteria that infect many insects; *Baumannia cicadellinicola* and *Sulcia muelleri*, the co-symbiotic bacteria of the glassy-winged sharpshooter (*Homalodisca coagulata*), which transmits the Pierce's disease pathogen *Xylella fastidiosa*; and eukaryotic protist (flagellate) endosymbionts in termites. Also see, for example, Wu et al. (2006) *PLoS Biol.*, 4(6):e188 doi:10.1371/journal.pbio.0040188; Moran and Telang (1998) *BioScience*, 48:295-304; and Moran and Baumann (2000) *Curr. Opin. Microbiol.*, 3:270-275. In an alternative approach, expression of an endogenous target gene of the invertebrate pest can be modified in such a way as to control a symbiont of the invertebrate, in turn affecting the host invertebrate. For example, it was reported that RNAi-mediated gene suppression using constructs (head-to-tail inverted repeats of the target gene including an intronic spacer) targetting the *Drosophila* homeobox gene *Caudal*, which represses nuclear factor kappa B-dependent antimicrobial peptide genes, led to overexpression of antimicrobial peptides, thus altering the commensal bacterial population in the *Drosophila* gut and eventually leading to gut cell apoptosis and host mortality; see Ryu et al (2008) *Science*, 319:777-782.

Pests of interest are described in detail in the section "Target Genes and Pest Invertebrates". Of particular interest are sapsucking insects, such as aphids, *Lygus*, leafhoppers, whiteflies, thrips, scale insects and mealybugs, as well as insects that ingest plant tissues or cells, such as lepidopteran larvae. Non-limiting embodiments include embodiments where (a) the plant is maize and the invertebrate pest is a *Diabrotica* species; (b) the plant is soybean and the invertebrate pest is a soybean cyst nematode (*Heterodera glycines*); (c) the plant is a grape and the invertebrate pest is a grape phylloxera or a glassy-winged sharpshooter (*Homalodisca coagulata*); and (d) the plant is an apple tree and the invertebrate pest is a woolly apple aphid.

In many embodiments, the recombinant DNA construct further includes one or more elements selected from: (a) a promoter functional in a plant cell; (b) a transgene transcription unit; (c) a gene suppression element; and (d) a transcription regulatory/transcript stabilizing element. Promoters useful in this invention have promoter activity in a plant cell. Suitable promoters include those described in detail under the heading "Promoters". Non-limiting examples of promoters include constitutive promoters, promoters with expression patterns in tissues likely to be contacted by the pest invertebrate (e.g., phloem-specific promoters, vascular-specific promoters, or root-specific promoters), and inducible promoters such as promoters that are induced by stress (abiotic stress or biotic stress such as stress from an infestation by the pest invertebrate).

A transgene transcription unit includes DNA sequence encoding a gene of interest. A gene of interest can include any coding or non-coding sequence from any species (including, but not limited to, non-eukaryotes such as bacteria, and viruses; fungi; protists, including protozoans; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a transgene transcription unit include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, RNA aptamers capable of binding to a ligand, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the cell (e.g., a plant cell) in which the recombinant DNA construct of the invention is to be transcribed, or can be a non-native gene. A gene of interest can be a marker gene, for example, a selectable marker gene encoding antibiotic, antifungal, or herbicide resistance, or a marker gene encoding an easily detectable trait (e.g., in a plant cell, phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention. Genes of interest include those genes also described above as target genes, under the heading "Target Genes". The transgene transcription unit can further include 5' or 3' sequence or both as required for transcription of the transgene.

Gene suppression elements include any DNA sequence (or RNA sequence encoded therein) designed to specifically suppress a gene or genes of interest. In the context of "gene suppression elements", "target gene" generally refers to a gene other than the target gene of the invertebrate pest silenced by the mature miRNA of this invention; this can be a gene endogenous to the transgenic plant cell or a gene exogenous to the plant. In the context of "gene suppression elements", non-limiting examples of suitable target genes also include amino acid catabolic genes (such as, but not limited to, the maize LKRISDH gene encoding lysine-ketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a transgenic plant or tissue of such a plant that is further improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575); all the patents cited in this paragraph are incorporated by reference in their entirety herein.

Suitable gene suppression elements are described in detail in U.S. Patent Application Publication 2006/0200878, which is incorporated herein by reference, and include one or more of:
  (a) DNA that includes at least one anti-sense DNA segment that is anti-sense to at least one segment of the target gene;
  (b) DNA that includes multiple copies of at least one anti-sense DNA segment that is anti-sense to at least one segment of the target gene;
  (c) DNA that includes at least one sense DNA segment that is at least one segment of the target gene;
  (d) DNA that includes multiple copies of at least one sense DNA segment that is at least one segment of the target gene;
  (e) DNA that transcribes to RNA for suppressing the target gene by forming double-stranded RNA and includes at least one anti-sense DNA segment that is anti-sense to at least one segment of the target gene and at least one sense DNA segment that is at least one segment of the target gene;
  (f) DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene;
  (g) DNA that transcribes to RNA for suppressing the target gene by forming multiple double strands of RNA and includes multiple anti-sense DNA segments that are anti-sense to at least one segment of the target gene and multiple sense DNA segments that are at least one segment of the target gene, and wherein the multiple anti-sense DNA segments and the multiple sense DNA segments are arranged in a series of inverted repeats;
  (h) DNA that includes nucleotides derived from a plant miRNA;
  (i) DNA that includes nucleotides of a siRNA;
  (j) DNA that transcribes to an RNA aptamer capable of binding to a ligand; and
  (k) DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer.

Figure 8:
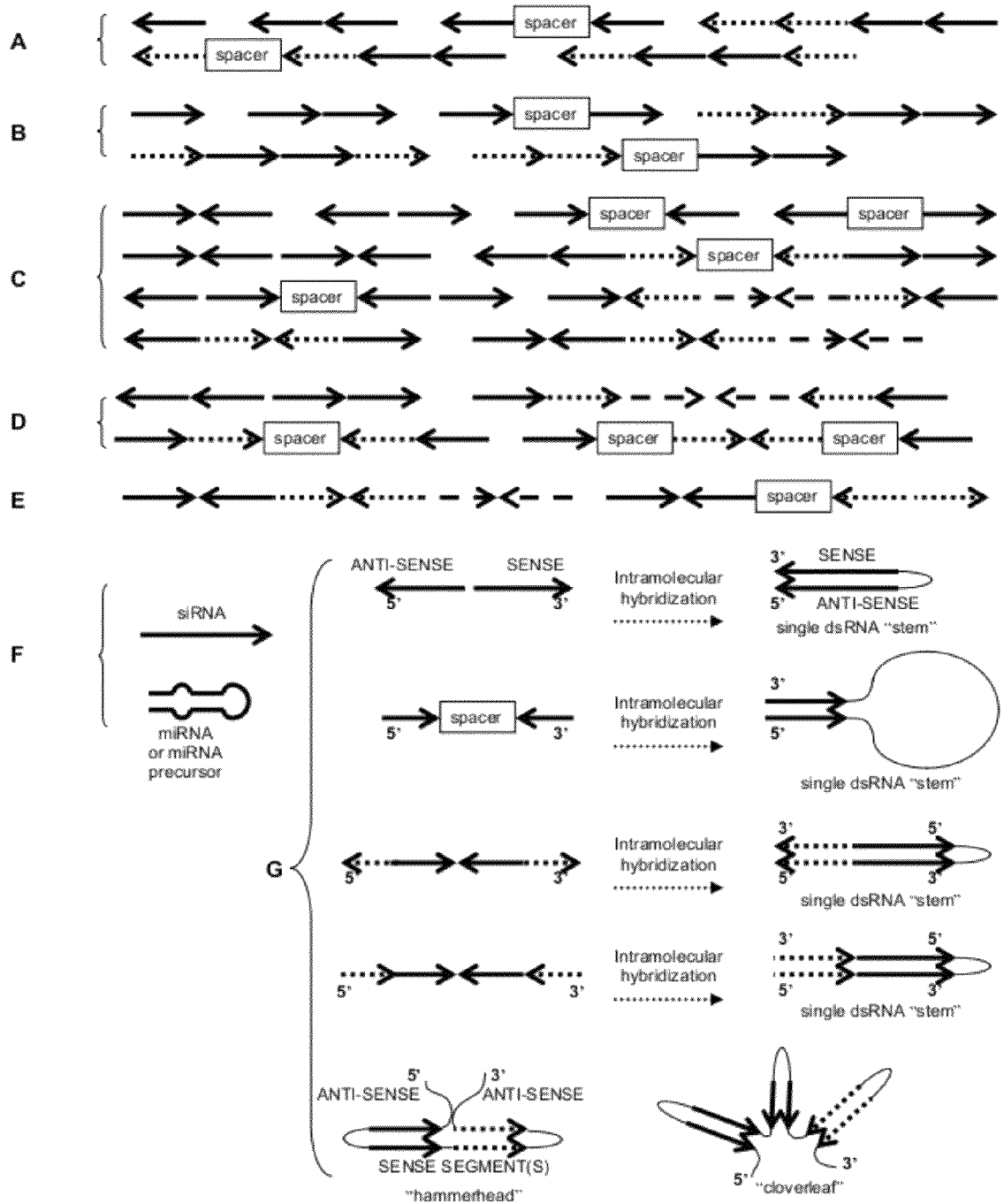
FIG. 8 depicts various non-limiting examples of gene suppression elements as described in Example 6. Where drawn as a single strand (FIGS. 6A through 6E), these are conventionally depicted in 5' to 3' (left to right) transcriptional direction, where the arrows indicate anti-sense sequence (arrowhead pointing to the left), or sense sequence (arrowhead pointing to the right). Where drawn as double-stranded (anti-parallel) transcripts (FIGS. 6F and 6G), the 5' and 3' transcriptional directionality is as shown. Solid lines, dashed lines, and dotted lines indicate sequences that target different target genes.

DNA elements for suppressing expression are described further in Example 6 and depicted in FIGS. 7 and 8.

Transcription regulatory elements include elements that regulate the expression level of the recombinant DNA construct of this invention (relative to its expression in the absence of such regulatory elements). Non-limiting examples of suitable transcription regulatory elements include riboswitches (cis- or trans-acting) and miRNA recognition sites, as described in detail in U.S. Patent Application Publication 2006/0200878, incorporated herein by reference. Other examples of transcription regulatory elements include transcript stabilizing elements such as an RNA that assumes a secondary structure or three-dimensional configuration (e.g., a loop, stem-loop, pseudoknot) that confers on the transcript increased stability or increased half-life in vivo; an RNA aptamer that confers on the transcript increased cell or tissue specificity; and transcript destabilizing elements such as the SAUR destabilizing sequences described in detail in U.S. Patent Application Publication 2007/0011761, incorporated herein by reference.

In some embodiments of this invention, the non-natural plant is a non-natural transgenic plant, such as one provided by techniques described below under the heading "Making and Using Transgenic Plant Cells and Transgenic Plants". In such embodiments, all cells (with the possible exception of haploid cells) and tissues of the non-natural plant contain the recombinant DNA construct of this invention.

In other embodiments, the non-natural plant is not completely transgenic, but includes natural non-transgenic tissue (for example, non-natural transgenic tissue grafted onto natural non-transgenic tissue). In a non-limiting embodiment, the non-natural plant includes a natural non-transgenic scion and a non-natural transgenic rootstock including the transgenic plant cell, wherein the non-transgenic scion and transgenic rootstock are grafted together. Such embodiments are particularly useful where the plant is one that is commonly vegetatively grown as a scion grafted onto a rootstock (wherein scion and rootstock can be of the same species or variety or of different species or variety); non-limiting examples include grapes (e.g., wine grapes and table grapes), apples, pears, quince, avocados, citrus, stone fruits (e.g., peaches, plums, nectarines, apricots, cherries), kiwifruit, roses, and other plants of agricultural or ornamental importance. Specifically claimed embodiments include embodiments where (a) the non-natural plant includes a natural non-transgenic grape scion and a non-natural transgenic grape rootstock and the invertebrate pest is a grape phylloxera; and (b) the non-natural plant includes a natural non-transgenic fruit tree (e.g., pear) scion and a non-natural transgenic fruit tree (e.g., quince) rootstock.

Target Genes and Pest Invertebrates

In one aspect, this invention provides a recombinant DNA construct that is transcribed in the transgenic plant cell to a recombinant miRNA precursor; wherein the recombinant miRNA precursor includes a single strand of RNA that folds into the secondary structure of an invertebrate miRNA precursor and that includes at least one stem-loop that is processed to a mature miRNA; and the mature miRNA suppresses expression of at least one target gene of the invertebrate pest, thereby conferring on the plant resistance to the invertebrate pest. The target gene of the invertebrate pest can be any target gene or genes of the invertebrate pest. The target gene can be a target gene of a symbiont associated with the invertebrate pest; suppression of such a symbiont gene confers on the plant resistance to the invertebrate pest. The target gene can include a single gene or part of a single gene that is targetted for suppression, or can include, for example, multiple consecutive segments of a target gene, multiple non-consecutive segments of a target gene, multiple alleles of a target gene, or multiple target genes from one or more species.

A target gene includes a sequence endogenous to any invertebrate pest species (or of a symbiont associated with the invertebrate pest). Of particular interest are arthropods (insects and arachnids), nematodes, molluscs (such as slugs or snails), annelids, and obligate symbionts of invertebrate pests. The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs (that is, the primary transcript encoding an endogenous microRNA, or the RNA intermediates processed from this primary transcript), small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124). Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

In many preferred embodiments, the target gene is an essential gene of the invertebrate pest (or of a symbiont associated with the invertebrate pest). Essential genes include genes that are required for development of the invertebrate pest to a fertile reproductive adult. Essential genes include genes that, when silenced or suppressed, result in the death of the invertebrate pest (as an adult or at any developmental stage, including gametes) or in the invertebrate pest's inability to successfully reproduce (e.g., sterility in a male or female parent or lethality to the zygote, embryo, or larva). A description of nematode essential genes is found, e.g., in Kemphues, K. "Essential Genes" (Dec. 24, 2005), Worm-Book, ed. The *C. elegans* Research Community, WormBook, doi/10.1895/wormbook.1.57.1, available on line at www-.wormbook.org. Soybean cyst nematode essential genes are disclosed in U.S. patent application Ser. No. 11/360,355, filed 23 Feb. 2006, incorporated by reference herein. Non-limiting examples of invertebrate essential genes include major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U.S. Patent Application Publication 2006/0021087 A1, PCT Patent Application PCT/US05/11816, and in Table II of U.S. Patent Application Publication 2004/0098761 A1, which are incorporated by reference herein. A description of insect genes is publicly available at the *Drosophila* genome database (available on line at flybase.bio.indiana.edu/). The majority of predicted *Drosophila* genes have been analyzed for function by a cell culture-based RNA interference screen, resulting in 438 essential genes being identified; see Boutros et al. (2004) *Science*, 303:832-835, and supporting material available on line at www.sciencemag.org/cgi/content/full/303/5659/832/DC1. Other examples of essential insect genes include a gut cell protein, a membrane protein, an ecdysone receptor, ATPases such as gamma-ATPase, an amino acid transporter, a transcription factor, a peptidylglycine alpha-amidating monooxygenase; a cysteine protease, an aminopeptidase, a dipeptidase, a sucrase/transglucosidase, a translation elongation factor, an eukaryotic translation initiation factor 1A, a splicing factor, an apoptosis inhibitor; a tubulin protein, an actin protein, an alpha-actinin protein, a histone, a histone deacetylase, a cell cycle regulatory protein, a cellular respiratory protein; a receptor for an insect-specific hormonal signal, a juvenile hormone receptor, an insect peptidic hormone receptor; a protein regulating ion balance in a cell, a proton-pump, a Na/K pump, an intestinal protease; an enzyme involved in sucrose metabolism, a digestive enzyme, a trypsin-like protease and a cathepsin B-like protease. Essential genes include those that influence other genes, where the overall effect is the death of the invertebrate pest or loss of the invertebrate pest's inability to successfully reproduce. In an non-limiting example, suppression of the *Drosophila* homeobox gene *Caudal* leads eventually to host mortality caused by an indirect effect (i.e., the disequilibrium of the insect's commensal gut bacterial population) (Ryu et al (2008) *Science*, 319:777-782) and thus *Caudal* as well as the antimicrobial peptide genes directly controlled by *Caudal* are both considered essential genes.

Plant pest invertebrates include, but are not limited to, nematodes, molluscs (slugs and snails), and insects and arachnids. See also G. N. Agrios, "Plant Pathology" (Fourth Edition), Academic Press, San Diego, 1997, 635 pp., for descriptions of nematodes and flagellate protozoans, all of which are invertebrate pests of interest. See also the continually updated compilation of plant pests and the diseases caused by such on the American Phytopathological Society's "Common Names of Plant Diseases", compiled by the Committee on Standardization of Common Names for Plant Diseases of The American Phytopathological Society, 1978-2005, available online at www.apsnet.org/online/common/top.asp.

Non-limiting examples of invertebrate pests include cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as phylloxera (*Daktulosphaira vitifoliae*), corn borers, cutworms, armyworms, leafhoppers, Japanese beetles, grasshoppers, and other pest coleopterans, dipterans, and lepidopterans. Specific examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), clay-backed cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is incorporated in its entirety by reference herein.

Invertebrate pests of particular interest, especially in but not limited to southern hemisphere regions (including South and Central America) include aphids, corn rootworms, spodoptera, noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*), "gusano aspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (*Mocis latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterranea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various thrips species (*Frankliniella* spp.), cotton earworm (*Helicoverpa zea*), "oruga bolillera" (e.g., *Helicoverpa geletopoeon*), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion thrips (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*), "oruga de la alfalfa" (*Colias lesbia*), "chinche marrón" or "chinche de los cuernos" (*Dichelops furcatus*), "alquiche chico" (*Edessa miditabunda*), blister beetles (*Epicauta* spp.), "barrenador del brote" (*Epinotia aporema*), "oruga verde del yuyo colorado" (*Loxostege bifidalis*), rootknot nematodes (*Meloidogyne* spp.), "oruga cuarteadora" (*Mocis repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines, Meloidogyne* spp., *Belonolaimus* spp.), bananas (*Radopholus similis, Meloidogyne* spp., *Helicotylenchus* spp.), sugarcane (*Heterodera sacchari, Pratylenchus* spp., *Meloidogyne* spp.), oranges (*Tylenchulus* spp., *Radopholus* spp., *Belonolaimus* spp., *Pratylenchus* spp., *Xiphinema* spp.), coffee (*Meloidogyne* spp., *Pratylenchus* spp.), coconut palm (*Bursaphelenchus* spp.), tomatoes (*Meloidogyne* spp., *Belonolaimus* spp., *Nacobbus* spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xiphinema* spp.), cacao (*Meloidogyne* spp., *Rotylenchulus reniformis*), pineapple (*Meloidogyne* spp., *Pratylenchus* spp., *Rotylenchulus reniformis*), papaya (*Meloidogyne* spp., *Rotylenchulus reniformis*), grapefruit (*Tylenchulus* spp., *Radopholus* spp. *Belonolaimus* spp., *Pratylenchus* spp., *Xiphinema* spp.), and broad beans (*Meloidogyne* spp.).

The recombinant DNA construct can be designed to be more specifically suppress the target gene, for example, by designing the recombinant DNA construct to encode a recombinant miRNA precursor that is processed to a mature miRNA that includes regions substantially non-complementary to a non-target gene sequence. Non-target genes can include any gene not intended to be silenced or suppressed, either in a plant containing the recombinant DNA construct or in organisms that may come into contact with the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a specific invertebrate pest species of interest, and the non-target gene is a gene or genes of one or more non-target species (such as a gene or genes of a plant species or a gene of a virus, fungus, bacterium, a non-target invertebrate, or vertebrate, even a human). One non-limiting example is where the recombinant DNA construct is designed to be processed to a mature miRNA for suppressing a target gene that is a gene endogenous to a single species (e.g., Western corn rootworm, *Diabrotica virgifera virgifera* LeConte) but not suppressing a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the recombinant DNA construct to be processed to a mature miRNA for suppressing a target gene sequence common to the multiple species in which the target gene is to be silenced. Thus, the miRNA processed from the recombinant DNA construct can be designed to be specific for one taxon (for example, specific to a genus, family, or even a larger taxon such as a phylum, e.g., arthropoda) but not for other taxa (e.g., plants or vertebrates or mammals). In one non-limiting example of this embodiment, the recombinant DNA construct can be designed to be processed to a mature miRNA for suppressing a target gene sequence common to aphids (Aphidoidea) but not target any gene sequence from other insects or invertebrates.

In another non-limiting example of this embodiment, a recombinant DNA construct for gene silencing in corn rootworm is designed to be processed to a mature miRNA for suppressing a target gene sequence common to all members of the genus *Diabrotica*. In a further example of this embodiment, such a *Diabrotica*-targetted recombinant DNA construct can be selected so as to not target any sequence from beneficial coleopterans (for example, predatory coccinellid beetles, commonly known as ladybugs or ladybirds) or other beneficial insect species.

The required degree of specificity of a recombinant DNA construct of this invention for silencing a target gene depends on various factors. Factors can include the size and nucleic acid sequence of the mature microRNA encoded by the recombinant DNA construct, and the relative importance of decreasing such a mature miRNA's potential to suppress non-target genes. In a non-limiting example, where such a mature miRNA is expected to be 22 base pairs in size, one particularly preferred embodiment includes DNA encoding a mature miRNA for silencing a target gene wherein the mature miRNA includes sequence that is substantially non-identical to a non-target gene sequence, such as fewer than 19, or fewer than 18, or fewer than 17, or fewer than 16, or fewer than 15 matches out of 22 contiguous nucleotides of a non-target gene sequence.

In some embodiments, it may be desirable to design the recombinant DNA construct to include regions predicted to not generate undesirable polypeptides, for example, by screening the recombinant DNA construct for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at www.iit.edu/~sgendel/fa.htm) (see also, for example, Gendel (1998) *Adv. Food Nutr. Res.,* 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (www.ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (www.ncbi.nih.gov/Entrez).

In one non-limiting example, the recombinant DNA construct is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene. In one embodiment the recombinant DNA construct is designed so no potential open reading frame that begins with AUG (ATG in the corresponding DNA) is included. Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in the recombinant DNA construct.

Applicants recognize that in some microRNA-mediated gene silencing, it is possible for imperfectly matching miRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.,* 23:3356-3364. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.,* 33:1671-1677). Thus, a given strand of the recombinant DNA construct need not always have 100% sequence identity with the intended target gene, but generally would preferably have substantial sequence identity with the intended target gene, such as about 95%, about 90%, about 85%, or about 80% sequence identity with the intended target gene. Described in terms of complementarity, one strand of the recombinant DNA construct is preferably designed to have substantial complementarity to the intended target (e.g., a target messenger RNA or target non-coding RNA), such as about 95%, about 90%, about 85%, or about 80% complementarity to the intended target. In a non-limiting example, in the case of a recombinant DNA construct encoding a mature miRNA of 22 nucleotides, the encoded mature miRNA is designed to be is substantially but not perfectly complementary to 22 contiguous nucleotides of a target RNA; preferably the nucleotide at position 22 is unpaired with the corresponding position in the target RNA to prevent transitivity.

Persons of ordinary skill in the art are capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, a recombinant DNA construct of this invention is designed to be processed to a mature miRNA that is active across several target invertebrate pest species, and therefore one skilled in the art can determine that it is more important to include in the recombinant DNA construct DNA encoding a mature miRNA that is specific to the several invertebrate pest species of interest, but less important to screen for regions predicted to have higher gene silencing efficiency or for regions predicted to generate undesirable polypeptides.

Promoters

Generally, the recombinant DNA construct of this invention includes a promoter, functional in a plant cell, and operably linked to the DNA encoding the recombinant miRNA precursor. In various embodiments, the promoter is selected from the group consisting of a constitutive promoter, a spatially specific promoter, a temporally specific promoter, a developmentally specific promoter, and an inducible promoter.

Non-constitutive promoters suitable for use with the recombinant DNA constructs of the invention include spatially specific promoters, temporally specific promoters, and inducible promoters. Spatially specific promoters can include organelle-, cell-, tissue-, or organ-specific promoters (e.g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e.g., water deficit or drought, heat, cold, high or low nutrient or salt levels, high or low light levels, or pest or pathogen infection). Of particular interest are microRNA promoters, especially those having a temporally specific, spatially specific, or inducible expression pattern. An expression-specific promoter can also include promoters that are generally constitutively expressed but at differing degrees or "strengths" of expression, including promoters commonly regarded as "strong promoters" or as "weak promoters".

Promoters of particular interest include the following non-limiting examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837, 848; 6,437,217 and 6,426,446; a maize L3 oleosin promoter disclosed in U.S. Pat. No. 6,433,252; a promoter for a plant nuclear gene encoding a plastid-localized aldolase disclosed in U.S. Patent Application Publication 2004/0216189; cold-inducible promoters disclosed in U.S. Pat. No. 6,084,089; salt-inducible promoters disclosed in U.S. Pat. No. 6,140, 078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/ 0123347 A1. All of the above-described patents and patent publications disclosing promoters and their use, especially in recombinant DNA constructs functional in plants are incorporated herein by reference.

Plant vascular- or phloem-specific promoters of interest include a rolC or rolA promoter of *Agrobacterium rhizogenes*, a promoter of a *Agrobacterium tumefaciens* T-DNA gene 5, the rice sucrose synthase RSs1 gene promoter, a *Commelina* yellow mottle badnavirus promoter, a coconut foliar decay virus promoter, a rice tungro bacilliform virus promoter, the promoter of a pea glutamine synthase GS3A gene, a invCD111 and invCD141 promoters of a potato invertase genes, a promoter isolated from *Arabidopsis* shown to have phloem-specific expression in tobacco by Kertbundit et al. (1991), a VAHOX1 promoter region, a pea cell wall invertase gene promoter, an acid invertase gene promoter from carrot, a promoter of a sulfate transporter gene Sultr1;3, a promoter of a plant sucrose synthase gene, and a promoter of a plant sucrose transporter gene.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol. Cell Biol.*, 5:451-463, Davidson and Ellington (2005) *Trends Biotechnol.*, 23:109-112, Winkler et al. (2002) *Nature*, 419: 952-956, Sudarsan et al. (2003) *RNA*, 9:644-647, and Mandal and Breaker (2004) *Nature Struct. Mol. Biol.*, 11:29-35. Such "riboregulators" could be selected or designed for specific spatial or temporal specificity, for example, to regulate translation of the DNA encoding the recombinant miRNA precursor only in the presence (or absence) of a given concentration of the appropriate ligand. One non-limiting example is a riboregulator that is responsive to an endogenous ligand (e.g., jasmonic acid or salicylic acid) produced by the plant when under stress (e.g., abiotic stress such as water, temperature, or nutrient stress, or biotic stress such as attach by pests or pathogens); under stress, the level of endogenous ligand increases to a level sufficient for the riboregulator to begin transcription of the DNA encoding the recombinant miRNA precursor.

Making and Using Recombinant DNA Constructs

The recombinant DNA constructs of this invention are made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, NY, 2001. An example of useful technology for building DNA constructs and vectors for transformation is disclosed in U.S. Patent Application Publication 2004/0115642 A1, incorporated herein by reference. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051, all of which are incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e.g., the first gene suppression element or the gene expression element) codon-optimized for expression in a plant by methods known in the art. See, e.g., U.S. Pat. No. 5,500,365, incorporated by reference, for a description of codon-optimization methodology for plants; see also De Amicis and Marchetti (2000) *Nucleic Acid Res.,* 28:3339-3346.

Transgenine Plant Cells and Plants

Another aspect of this invention provides a non-natural transgenic plant cell having in its genome recombinant DNA that is transcribed in the non-natural transgenic plant cell to a recombinant miRNA precursor, wherein the recombinant miRNA precursor includes a single strand of RNA that folds into the secondary structure of an invertebrate miRNA precursor and that includes at least one stem-loop that is processed to a mature miRNA, and wherein the mature miRNA suppresses expression of at least one target gene of an invertebrate or of a symbiont associated with the invertebrate. Also provided are a non-natural transgenic plant containing the non-natural transgenic plant cell of this invention, a non-natural transgenic plant grown from the non-natural transgenic plant cell of this invention, and non-natural transgenic seed produced by the non-natural transgenic plants. Such non-natural transgenic plant cells, plants, and seeds can be made using the techniques described below under the heading "Making and Using Transgenic Plant Cells and Transgenic Plants". This invention further provides a method of suppressing at least one target gene of an invertebrate pest of a plant or of a symbiont associated with the invertebrate, including providing a plant including the non-natural transgenic plant cell of this invention, wherein the invertebrate is the invertebrate pest, the recombinant DNA is transcribed in the non-natural transgenic plant cell to the recombinant miRNA precursor, and when the invertebrate pest ingests the recombinant miRNA precursor, the at least one target gene is suppressed.

The non-natural transgenic plant of this invention includes plants of any developmental stage, and includes a non-natural regenerated plant prepared from the non-natural transgenic plant cells disclosed herein, or a non-natural progeny plant (which can be an inbred or hybrid progeny plant) of the regenerated plant, or seed of such a non-natural transgenic plant. Also provided and claimed is a non-natural transgenic seed having in its genome a recombinant DNA construct of this invention. The non-natural transgenic plant cells, transgenic plants, and transgenic seeds of this invention are made by methods well-known in the art, as described below under the heading "Making and Using Transgenic Plant Cells and Transgenic Plants".

The non-natural transgenic plant cell can include an isolated plant cell (e.g., individual plant cells or cells grown in or on an artificial culture medium), or can include a plant cell in undifferentiated tissue (e.g., callus or any aggregation of plant cells). The non-natural transgenic plant cell can include a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules).

The non-natural transgenic plant cell or non-natural transgenic plant of the invention can be any suitable plant cell or plant of interest. Both transiently transformed and stably transformed plant cells are encompassed by this invention. Stably transformed transgenic plants are particularly preferred. In many preferred embodiments, the non-natural transgenic plant is a fertile transgenic plant from which seed can be harvested, and the invention further claims non-natural transgenic seed of such transgenic plants, wherein the non-natural seed preferably also contains the recombinant construct of this invention.

Making and Using Transgenic Plant Cells and Transgenic Plants

Where a recombinant DNA construct of this invention is used to produce a non-natural transgenic plant cell, transgenic plant, or transgenic seed of this invention, transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize), all of which are incorporated by reference.

Another preferred method of plant transformation is *Agrobacterium*-mediated transformation. In one preferred embodiment, the transgenic plant cell of this invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135, incorporated by reference. Also see De Framond (1983) *Biotechnology,* 1:262-269; and Hoekema et al., (1983) *Nature,* 303:179. In such abinary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. Nos. 5,591,616 and 5,981,840 (maize); U.S. Pat. No. 5,463,174 (brassicas), and in U.S. Patent Application Publication 2004/0244075 (maize), all of which are incorporated by reference. Similar methods have been reported for many plant species, both dicots and monocots, including, among others, peanut (Cheng et al. (1996) *Plant Cell Rep.,* 15: 653); asparagus (Bytebier et al. (1987) *Proc. Natl. Acad. Sci. U.S.A.,* 84:5345); barley (Wan and Lemaux (1994) *Plant Physiol.,* 104:37); rice (Toriyama et al (1988) *Bio/Technology,* 6:10; Zhang et al (1988) *Plant Cell Rep.,* 7:379; wheat (Vasil et al. (1992) *Bio/Technology,* 10:667; Becker et al. (1994) *Plant J.,* 5:299), alfalfa (Masoud et al (1996) *Transgen. Res.,* 5:313); and tomato (Sun et al. (2006) *Plant Cell Physiol.,* 47:426-431). See also a description of vectors, transformation methods, and production of transformed *Arabidopsis thaliana* plants where transcription factors are constitutively expressed by a CaMV35S promoter, in U.S. Patent Application Publication 2003/0167537 A1, incorporated by reference. Transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are incorporated by reference.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047, all of which are incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring transcription of the recombinant DNA construct in the transgenic plant cell of the invention can be achieved by any suitable method, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Pena (editor) "Transgenic Plants: Methods and Protocols", Humana Press, 2004.

Other suitable methods for detecting or measuring transcription of the recombinant DNA construct in the transgenic plant cell of the invention include measurement of any other trait that is a direct or proxy indication of suppression of the target gene in the transgenic plant cell in which the recombinant DNA construct is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., in plants, these assays include plant part assays such as leaf or root assays to determine tolerance of abiotic stress). Non-limiting methods include direct measurements of resistance to the invertebrate pest (e.g., damage to plant tissues) or proxy assays (e.g., plant yield assays, or bioassays such as the Western corn rootworm (*Diabrotica virgifera virgifera* LeConte) larval bioassay described in International Patent Application Publication WO2005/110068 A2 and U.S. Patent Application Publication US 2006/0021087 A1, incorporated by reference, or the soybean cyst nematode bioassay described by Steeves et al. (2006) *Funct. Plant Biol.*, 33:991-999, wherein cysts per plant, cysts per gram root, eggs per plant, eggs per gram root, and eggs per cyst are measured.

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, incorporated by reference.

Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a transgenic plant grown from the transgenic seed of the invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:
(a) plant seeds of the first parent plant (e.g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491, each of which is incorporated by reference in their entirety.

In certain transgenic plant cells and transgenic plants of the invention, it may be desirable to concurrently express (or suppress) a gene of interest while also regulating expression of a target gene. Thus, in some embodiments, the transgenic plant contains recombinant DNA further including a gene expression (or suppression) element for expressing at least one gene of interest, and transcription of the recombinant miRNA precursor is preferably effected with concurrent transcription of the gene expression (or suppression) element.

Thus, as described herein, the non-natural transgenic plant cells or transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, broccoli, cabbage, carrot, cauliflower, Chinese cabbage, cucumber, dry beans, eggplant, fennel, garden beans, gourds, lettuces, melons, okra, peas, peppers, pumpkin, radishes, spinach, squash, watermelon, cotton, potato, quinoa, amaranth, buckwheat, safflower, soybean, sugarbeet, and sunflower. Preferred monocots include, but are not limited to, wheat, oat, barley, maize (including sweet corn and other varieties), rye, triticale, rice, ornamental and forage grasses, sorghum, millet, onions, leeks, and sugarcane, more preferably maize, wheat, and rice.

The ultimate goal in plant transformation is to produce plants which are useful to man. In this respect, non-natural transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338, incorporated by reference, and PCT Publications WO 95/06128 and WO 02/057471. Thus, this invention also provides commodity products produced from a non-natural transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a non-natural transgenic plant cell, plant, or seed of this invention.

In preferred embodiments, the non-natural transgenic plant prepared from the non-natural transgenic plant cell of this invention, i.e., a non-natural transgenic plant having in its genome a recombinant DNA construct of this invention has at least one additional altered trait, relative to a plant lacking the recombinant DNA construct, selected from the group of traits consisting of:
 (a) improved abiotic stress tolerance;
 (b) improved biotic stress tolerance;
 (c) modified primary metabolite composition;
 (d) modified secondary metabolite composition;
 (e) modified trace element, carotenoid, or vitamin composition;
 (f) improved yield;
 (g) improved ability to use nitrogen or other nutrients;
 (h) modified agronomic characteristics;
 (i) modified growth or reproductive characteristics; and
 (j) improved harvest, storage, or processing quality.

In particularly preferred embodiments, the non-natural transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, non-natural transgenic seed, or seed produced by the non-natural transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc), carotenoid (e.g., beta-carotene, lycopene, lutein, zeaxanthin, or other carotenoids and xanthophylls), or vitamin (e.g., tocopherols,) composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e.g., peanut allergens including ara h 1, wheat allergens including gliadins and glutenins, soy allergens including P34 allergen, globulins, glycinins, and conglycinins) or of a toxic metabolite (e.g., cyanogenic glycosides in cassava, solanum alkaloids in members of the Solanaceae).

EXAMPLES

Example 1

This example describes non-limiting embodiments of recombinant DNA constructs useful in making the non-natural transgenic plant cells, plants, and seeds of this invention. More particularly, this example describes a recombinant DNA construct that is transcribable in a plant cell to a recombinant miRNA precursor, wherein the recombinant miRNA precursor includes a single strand of RNA that folds into the secondary structure of an invertebrate miRNA precursor and that includes at least one stem-loop that is processed to a mature miRNA; and wherein the mature miRNA is designed to suppress expression of at least one target gene of an invertebrate or of a symbiont associated with the invertebrate. This construct transcribes to a recombinant miRNA precursor that is relatively stable in planta, allowing ingestion of the relatively intact recombinant miRNA precursor by an invertebrate.

In one non-limiting embodiment of this invention, the recombinant DNA construct includes sequence derived from multiple miRNA precursors, e.g., a polycistronic cluster of 8 miRNAs ("8-mir") identified on chromosome 2R in *Drosophila melanogaster* as reported by Biemar et al. (2005) *Proc. Natl. Acad. Sci. U.S.A.*, 102:15907-15911. Using multiple miRNA precursors (multiple different precursors, or multiple copies of the same precursor, or combinations thereof) results in multiple mature miRNAs processed from a single recombinant DNA construct, which is advantageous for targeting multiple target genes (e.g., different alleles, different regions within a single target gene, or different target genes) or increasing the amount of mature miRNA available for silencing.

The "8-mir" cluster (SEQ ID NO. 1) is depicted in FIG. 1, with the individual miRNA precursors indicated by bold underlined text. A shorter sequence that includes all 8 miRNA precursors is also provided in SEQ ID NO. 2. This cluster includes DNA sequence encoding 8 miRNA precursors, arranged in this order: dme-mir-309 (SEQ ID NO. 3), dme-mir-3 (SEQ ID NO. 4), dme-mir-286 (SEQ ID NO. 5), dme-mir-4 (SEQ ID NO. 6), dme-mir-5 (SEQ ID NO. 7), dme-mir-6-1 (SEQ ID NO. 8), dme-mir-6-2 (SEQ ID NO. 9), and dme-mir-6-3 (SEQ ID NO. 10). Table 1 identifies the DNA sequence and corresponding RNA sequence for each miRNA precursor. The fold-back structure (that is, the secondary structure of the miRNA precursor including a stem-loop that is processed to the mature miRNA) for each of the 8 miRNA precursors is depicted in FIG. 2, in which the mature miRNA is indicated within the fold-back structure in bold capitals.

TABLE 1

| miRNA precursor | DNA sequence | RNA sequence |
| --- | --- | --- |
| dme-mir-309 | SEQ ID NO. 3 | SEQ ID NO. 11 |
| dme-mir-3 | SEQ ID NO. 4 | SEQ ID NO. 12 |
| dme-mir-286 | SEQ ID NO. 5 | SEQ ID NO. 13 |
| dme-mir-4 | SEQ ID NO. 6 | SEQ ID NO. 14 |
| dme-mir-5 | SEQ ID NO. 7 | SEQ ID NO. 15 |
| dme-mir-6-1 | SEQ ID NO. 8 | SEQ ID NO. 16 |
| dme-mir-6-2 | SEQ ID NO. 9 | SEQ ID NO. 17 |
| dme-mir-6-3 | SEQ ID NO. 10 | SEQ ID NO. 18 |

In one embodiment, a recombinant DNA construct including a sequence identical to (or substantially similar to) the "8-miR" sequence (SEQ ID NO. 1) is expressed in a transgenic plant cell under the control of a promoter that differs from the native promoter of the native *D. melanogaster* "8-miR" cluster precursor. The target gene is the endogenous target of the mature miRNAs natively processed from the "8-miR" cluster, or a gene including sequence similar to the endogenous target (e.g., homologues or orthologues of the endogenous target). Techniques for predicting a target of a given animal miRNA are known in the art and include those described by Lewis et al (2005) *Cell*, 120:15-16, Lewis et al. (2003) *Cell*, 115:787-798, and Rehmsmeier et al. (2004) *RNA*, 10:1507-1517. A publicly available target predictor, TargetScanS (www.targetscan.org), predicts biological targets of miRNAs by searching for the presence of conserved 8mer and 7mer sites that match the seed region (positions 2-7 of a mature miRNA) of each miRNA. Another publicly available on-line target predictor is RNAhybrid (bibiserv.techfak.uni-bielefeld.de/rnahybrid; see Krüger and Rehmsmeier (2006) *Nucleic Acids Res.*, 34:W451-W454, and Rehmsmeier et al. (2004) *RNA*, 10:1507-1517). Also publicly available is an integrated database, miRGen (www.diana.pcbi.upenn.edu/miRGen; see Megraw et al (2007) *Nucleic Acids Res.*, 35:D149-D155) that provides (i) positional relationships between animal miRNAs and genomic annotation sets and (ii) animal miRNA targets according to combinations of widely used target prediction programs. Also publicly available is TarBase (www.diana.pcbi.upenn.edu/tarbase; see Sethupathy et al. (2006) *RNA*, 12:192-197), a manually curated database of experimentally tested miRNA targets, in human/mouse, fruit fly, worm, and zebrafish, which distinguishes between miRNA targets that have been validated (tested positive) and those that tested negative.

In another embodiment, the "8-miR" sequence (SEQ ID NO. 1) serves as a template from which an "engineered 8-miR" sequence is derived, wherein the starting sequence is modified to yield derivative engineered miRNA precursors that are processed to engineered mature miRNAs designed to silence a specific target gene or genes other than the endogenous target(s) of the mature miRNAs natively processed from the "8-miR" cluster. Designing an artificial or engineered miRNA sequence can be as simple as substituting sequence that is complementary to the intended target for nucleotides in the miRNA stem region of the miRNA precursor, as demonstrated by Zeng et al. (2002) *Mol. Cell*, 9:1327-1333. One non-limiting example of a general method for determining nucleotide changes in the native miRNA sequence to produce the engineered miRNA precursor includes the following steps:

(a) Selecting a unique target sequence of at least 18 nucleotides specific to the target gene, e.g., by using sequence alignment tools such as BLAST (see, for example, Altschul et al. (1990) *J. Mol. Biol.*, 215:403-410; Altschul et al. (1997) *Nucleic Acids Res.*, 25:3389-3402), for example, of both maize cDNA and genomic DNA databases, to identify target transcript orthologues and any potential matches to unrelated genes, thereby avoiding unintentional silencing of non-target sequences.

(b) Analyzing the target gene for undesirable sequences (e.g., matches to sequences from non-target species), and score each potential 19-mer segment for GC content, Reynolds score (see Reynolds et al. (2004) *Nature Biotechnol.*, 22:326-330), and functional asymmetry characterized by a negative difference in free energy ("ΔΔG") (see Khvorova et al. (2003) *Cell*, 115:209-216). Preferably 19-mers are selected that have all or most of the following characteristics: (1) a Reynolds score >4, (2) a GC content between about 40% to about 60%, (3) a negative AAG, (4) a terminal adenosine, (5) lack of a consecutive run of 4 or more of the same nucleotide; (6) a location near the 3' terminus of the target gene; (7) minimal differences from the miRNA precursor transcript. Preferably multiple (3 or more) 19-mers are selected for testing. Positions at every third nucleotide in an siRNA have been reported to be especially important in influencing RNAi efficacy and an algorithm, "siExplorer" is publicly available at rna.chem.t.u-tokyo.acjp/siexplorer.htm (see Katoh and Suzuki (2007) *Nucleic Acids Res.*, 10.1093/nar/gkl1120).

(c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript.

(d) Testing the engineered miRNA precursor, for desirable characteristics, such as in planta stability, or efficacy in controlling the invertebrate pest. For example, a recombinant DNA construct containing the engineered miRNA precursor is expressed in plants under either a constitutive (e.g., CaMV 35S) or tissue-specific (e.g., root) promoter and in planta stability of the precursor is measured. In another example, the engineered miRNA precursor can be tested in a bioassay for larval mortality as a proxy measurement of target gene silencing efficacy; see, for example, the Western corn rootworm (*Diabrotica virgifera virgifera* LeConte) larval bioassay described in detail in International Patent Application Publication WO2005/110068 A2 and U.S. Patent Application Publication US 2006/0021087 A1, incorporated by reference. In yet another example, the engineered miRNA precursor can be tested in a soybean cyst nematode bioassay such as that described in detail by Steeves et al. (2006) *Funct. Plant Biol.,* 33:991-999, wherein cysts per plant, cysts per gram root, eggs per plant, eggs per gram root, and eggs per cyst are measured.

and (e) Cloning the most effective engineered miRNA precursor into a construct for stable transformation of a plant, e.g., maize (see the sections under the headings "Making and Using Recombinant DNA Constructs" and "Making and Using Transgenic Plant Cells and Transgenic Plants").

In a non-limiting example of the engineered miRNA approach, an "8-miR" sequence (SEQ ID NO. 1) was engineered to be processed to novel mature miRNAs designed to silence a *Diabrotica virgifera* vacuolar ATPase (vATPase, SEQ ID NO. 19). The mature miRNA sequences were designed taking into account what is currently known about animal miRNA processing, see, for example, Schwarz et al. (2003) *Cell,* 115:199-208, Khvorova et al. (2003) *Cell,* 115: 209-216, and Reynolds et al. (2004). *Nature Biotechnol.,* 22:326-330. Perfect or near perfect matches to the target sequence were selected for minimal off-target effects and maximum predicted efficacy. Each engineered mature miRNA sequence was designed to replace the corresponding endogenous mature miRNA, while preserving the predicted secondary structure of the precursor and the "8-miR" cluster. Table 2 lists each of the eight selected target sequences, its location within SEQ ID NO. 19, relevant properties of each target sequence, and the engineered miRNA sequence designed to silence the target sequence. The secondary structure (i.e., fold-back structure) of each native miRNA precursor was maintained in the corresponding engineered miRNA, which is depicted in FIG. 3.

The eight engineered miRNA sequences were substituted into the scaffold (native) "8-miR" cluster to yield a single engineered "8mirvATPase" sequence (SEQ ID NO. 44). Due to the method of construction, five variant 8mirvATPase sequences (each slightly different from SEQ ID NO. 44) were obtained, including variants "8mirvATPase-11" (SEQ ID NO. 45) and "8mirvATPase-16" (SEQ ID NO. 46). RNA of each of the five versions of 8mirvATPase was expressed from its corresponding plasmid and tested in a Western corn rootworm (WCR, *Diabrotica virgifera*) larval diet bioassay (described in U.S. Patent Application Publication US 2006/0021087 A1, incorporated by reference). All five RNAs showed some mortality and stunting against WCR larvae. RNA from constructs pMON97871 (containing SEQ ID NO. 45) and pMON97872 (containing SEQ ID NO. 46) caused significant WCR larval mortality of 64% and 77%, respectively, and were engineered for transcription in maize plants.

To test in planta stability of the engineered miRNA precursor transcripts, plasmid pMON97878 (including SEQ ID NO. 46 under the control of the CaMv35S promoter) was made and infiltrated into tobacco (*Nicotiana benthamiana*) plants. After three days, total RNA was extracted from three separate infiltrated plants and assayed by Northern blots using a digoxygenin-labelled RNA probe complementary to "8mirvATPase-16". The Northern blot (FIG. 4) showed that "8mirvATPase-16" (SEQ ID NO. 46) RNA was present in tobacco plants as both full-length "8mirvATPase-16" transcript and as degraded RNA, demonstrating that "8mirvATPase-16" RNA is more stable in plants than is the corresponding double-stranded RNA produced from an inverted repeat (i.e., sense adjacent to anti-sense of the same target gene), which was found to be entirely cleaved to small RNAs in planta (data not shown).

To assess efficacy at conferring on the plant resistance to the invertebrate pest, plasmids pMON97875, containing "8mirvATPase-11" (SEQ ID NO. 45), and pMON97876, containing "8mirvATPase-16" (SEQ ID NO. 46), were cloned using a maize binary plasmid. These plasmids were transformed into maize. The resulting plants are expected to display resistance to damage by Western corn rootworm.

TABLE 2

| Target sequence | Start and end base of SEQ ID NO. 19 | GC % | Reynolds' score | Sense 5' mfe* | Anti-sense 5' mfe* | ΔΔG | Scaffold miRNA precursor | DNA encoding engineered miRNA precursor | engineered miRNA precursor |
|---|---|---|---|---|---|---|---|---|---|
| GACTGGCTTGGATCATATT (SEQ ID NO. 20) | 1423-1441 | 42.1 | 7 | -9.2 | -4.7 | -4.5 | mir309 (SEQ ID NO. 11) | SEQ ID NO. 28 | mir309vATPase1423 (SEQ ID NO. 36) |
| GAGCATTGGACGACTTTTA (SEQ ID NO. 21) | 1454-1472 | 42.1 | 8 | -10.6 | -4.7 | -5.9 | mir3 (SEQ ID NO. 12) | SEQ ID NO. 29 | mir3vATPase1454 (SEQ ID NO. 37) |

TABLE 2-continued

| Target sequence | Start and end base of SEQ ID NO. 19 | GC % | Reynolds' score | Sense 5' mfe* | Anti-sense 5' mfe* | ΔΔG | Scaffold miRNA precursor | DNA encoding engineered miRNA precursor | engineered miRNA precursor |
|---|---|---|---|---|---|---|---|---|---|
| TGTGCAGCTGGTAGGTAAA (SEQ ID NO. 22) | 1554-1572 | 47.4 | 7 | -10.6 | -6.0 | -4.6 | mir286 (SEQ ID NO. 13) | SEQ ID NO. 30 | mir286vATPase1554 (SEQ ID NO. 38) |
| TGGCAGAAACGGACAAAAT (SEQ ID NO. 23) | 1580-1598 | 42.1 | 7 | -11.5 | -4.4 | -7.1 | mir4 (SEQ ID NO. 14) | SEQ ID NO. 31 | mir4vATPase1580 (SEQ ID NO. 39) |
| TGCCAGGCTTCTTAAAGAA (SEQ ID NO. 24) | 1611-1629 | 42.1 | 8 | -11.5 | -6.7 | -4.8 | mir5 (SEQ ID NO. 15) | SEQ ID NO. 32 | mir5vATPase1611 (SEQ ID NO. 40) |
| GCAGGCCTTCAGAAACTTA (SEQ ID NO. 25) | 1905-1923 | 47.4 | 8 | -11.2 | -6.8 | -4.4 | mir6-1 (SEQ ID NO. 16) | SEQ ID NO. 33 | mir6.1vATPase1905 (SEQ ID NO. 41) |
| TGGCCGTACTAAAGATAGT (SEQ ID NO. 26) | 2046-2064 | 42.1 | 7 | -12.6 | -6.8 | -5.8 | mir6-2 (SEQ ID NO. 17) | SEQ ID NO. 34 | mir6.2vATPase2046 (SEQ ID NO. 42) |
| GAGGGTACAGTGCTTATTA (SEQ ID NO. 27) | 2153-2171 | 42.1 | 8 | -11.2 | -5.0 | -6.2 | mir6-3 (SEQ ID NO. 18) | SEQ ID NO. 35 | mir6.3vATPase2153 (SEQ ID NO. 43) |

*mfe, minimum folding energy, a measure of the strongest pairing interacting between two sequences measured as ΔG Example 2

This example describes non-limiting embodiments including novel invertebrate miRNA precursors. More particularly, this example describes novel mature miRNA sequences and their corresponding miRNA precursor sequences and fold-back structures, identified from soybean cyst nematode (SCN, *Heterodera glycines*). The nematode miRNA precursors are useful in making recombinant DNA constructs useful in making the non-natural transgenic plant cells, plants, and seeds of this invention, especially non-natural transgenic soybean plants having resistance to SCN and other nematode or invertebrate pests. Ingestion of nematode-specific miRNAs (whether as an exogenously expressed native sequence or as an engineered miRNA) by nematodes (e.g., SCN) is envisioned as a method of controlling nematode and other invertebrate pests.

A library of small RNAs from soybean cyst nematode (*Heterodera glycine*, SCN) was constructed by standard procedures similar to those described in Aravin and Tuschl (2005) *FEBS Letts.*, 579:5830-5840 and Ambros and Lee (2004) *Methods Mol. Bio.*, 265:131-158. In brief, total RNA was isolated from SCN by the Trizol (Invitrogen) method. SCN RNA was fractionated on a polyacrylamide gel and small RNAs (about 18 to about 26 nucleotides) were eluted from the gel. Adaptors were ligated to the 5' and 3' ends of the small RNAs and the resulting ligation mixture was amplified by polymerase chain reaction (PCR). The PCR product was ligated into pCR2.1-TOPO vector (Invitrogen). The ligation mixture was transformed into *E. coli*. One hundred ninety-two resulting transformed colonies were grown and plasmid DNA was prepared from each colony. A partial DNA sequence was determined for each plasmid to determine the nature of the small RNA inserted into the vector.

Figure 5:
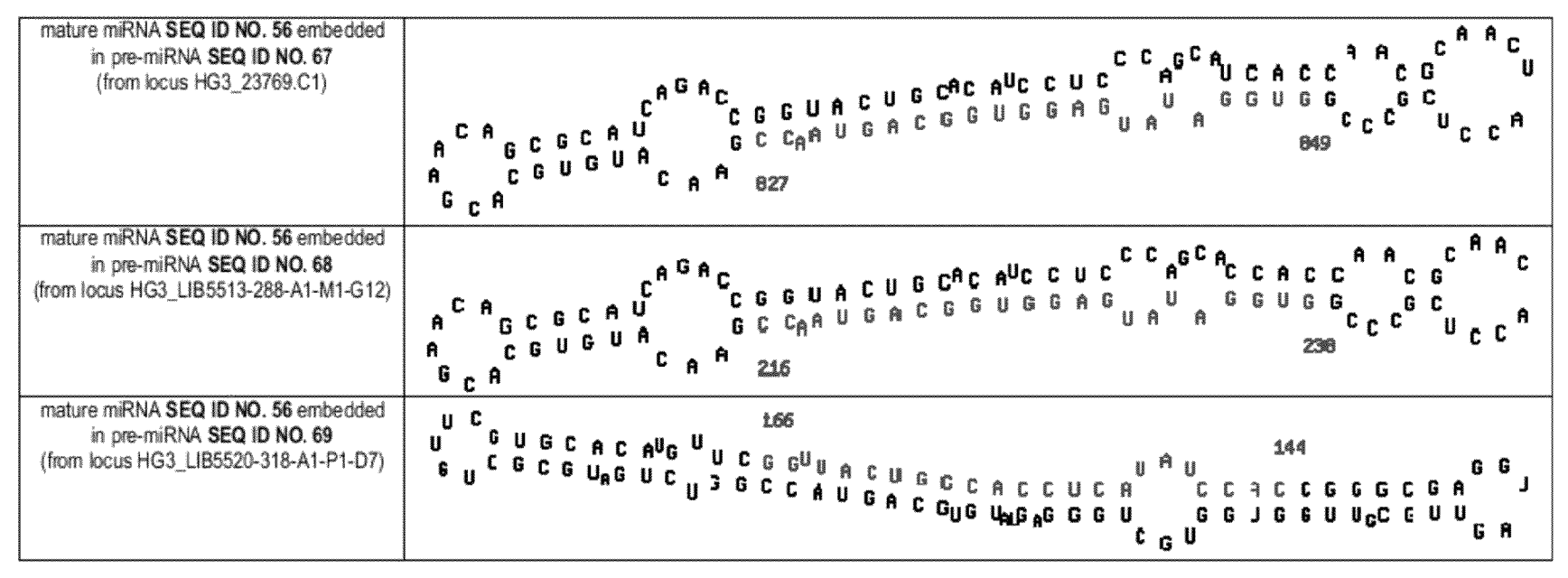

Two libraries were sequenced using conventional methods and 192 raw sequences were obtained. Eighty-nine unique small RNAs of about 18 to about 26 nucleotides in length were retrieved and analyzed for new miRNAs. New miRNAs were predicted by first folding the secondary structure using the RNAfold program in the Vienna package as described by Hofacker et al. (1994) *Monatsh. f Chemie*, 125:167-188. The structures thus predicted were filtered based on characteristics of validated miRNA precursors modified from those derived by Jones-Rhoades et al. (2006) *Annu. Rev. Plant. Biol.*, 57:19-53. Finally the prediction result was manually inspected. SCN homologues to four published miRNA families were identified and are listed in Table 3. Additionally, from 52 SCN genomic loci, 4 novel SCN miRNAs were predicted and given the trivial identifiers "SCN15" (GUCAGCCGAUCCUAAGGCACC, SEQ ID NO. 53), "SCN25" (UGGUGCGUGGACUAGUGGUGAG, SEQ ID NO. 54), "SCN30" (UGAAAGACAUGGGUAGUAUGAGACG, SEQ ID NO. 55), and "SCN31" (CACCUAUACUCCACCGUCAUUGG, SEQ ID NO. 56). The mature SCN miRNAs and their corresponding miRNA precursors are listed in Table 4. Non-limiting examples of fold-back structures (i.e., secondary structures of invertebrate miRNA precursors, each including at least one stem-loop that is processed to a mature miRNA, wherein the stem-loop includes a stem region and a loop region) are depicted in FIG. 5.

TABLE 3

| miRNA family | SCN sequence | SEQ ID NO. |
|---|---|---|
| miR-8 | UAAUACUGUCAGGUAAAGAUGUC | 47 |
| miR-71 | UGAAAGACAUGGGUAGUAUGAGACG | 48 |
| miR_86 | UAAGUGAAUUCUUUGCCACAGUCU | 49 |
| miR-100 | AACCCGUAGAUCCGAACUAGUC | 50 |
| miR-100 | AACCCGUAGAUCCGAACUAGUCU | 51 |
| miR-100 | AACCCGUAGAUCCGAACUUGUG | 52 |

TABLE 4

| SCN mature miRNA | mature miRNA SEQ ID NO. | Nucleotide position of mature miRNA in pre-miRNA start | Nucleotide position of mature miRNA in pre-miRNA end | Pre-miRNA SEQ ID NO | Nucleotide position of pre-miRNA in genomic locus start | Nucleotide position of pre-miRNA in genomic locus end | SCN genomic locus |
|---|---|---|---|---|---|---|---|
| 15 | 53 | 59 | 79 | 57 | 181 | 270 | HG3_LIB5513-477-A1-M1-H4 |
| 25 | 54 | 43 | 64 | 58 | 197 | 271 | HG3_34113.C1 |
| 25 | 54 | 43 | 64 | 58 | 197 | 271 | HG3_29652.C1 |
| 25 | 54 | 43 | 64 | 58 | 197 | 271 | HG3_28454.C1 |
| 25 | 54 | 43 | 64 | 59 | 197 | 271 | HG3_18268.C1 |
| 25 | 54 | 43 | 64 | 58 | 197 | 271 | HG3_34533.C1 |
| 25 | 54 | 43 | 64 | 58 | 172 | 246 | HG3_19260.C1 |
| 25 | 54 | 43 | 64 | 58 | 103 | 177 | HG3_25275.C1 |
| 25 | 54 | 43 | 64 | 60 | 103 | 177 | HG3_12307.C1 |
| 25 | 54 | 43 | 64 | 58 | 197 | 271 | HG3_25338.C1 |
| 25 | 54 | 43 | 64 | 58 | 197 | 271 | HG3_10253.C1 |
| 25 | 54 | 43 | 64 | 58 | 154 | 228 | HG3_29286.C1 |
| 25 | 54 | 43 | 64 | 58 | 197 | 271 | HG3_254.C1 |
| 25 | 54 | 43 | 64 | 58 | 156 | 230 | HG3_8212.C1 |
| 25 | 54 | 43 | 64 | 59 | 197 | 271 | HG3_18844.C1 |
| 25 | 54 | 43 | 64 | 61 | 63 | 137 | HG3_1908.C2 |
| 25 | 54 | 43 | 64 | 58 | 197 | 271 | HG3_33191.C1 |
| 25 | 54 | 43 | 64 | 59 | 197 | 271 | HG3_LIB5513-515-A1-P1-C7 |
| 25 | 54 | 43 | 64 | 58 | 197 | 271 | HG3_LIB5519-246-A1-M1-A2 |
| 25 | 54 | 43 | 64 | 59 | 35 | 109 | HG3_LIB5520-450-A1-P1-D6 |
| 25 | 54 | 43 | 64 | 58 | 197 | 271 | HG3_LIB5519-364-A1-M1-C2 |
| 25 | 54 | 43 | 64 | 58 | 197 | 271 | HG3_LIB5513-505-A2-M1-E11 |
| 25 | 54 | 43 | 64 | 62 | 197 | 271 | HG3_LIB5513-708-A1-M1-E9 |
| 25 | 54 | 43 | 64 | 59 | 197 | 271 | HG3_LIB5513-353-A1-P1-B11 |
| 25 | 54 | 43 | 64 | 59 | 197 | 271 | HG3_LIB5513-678-A1-M1-E6 |
| 25 | 54 | 43 | 64 | 63 | 76 | 150 | HG3_LIB5513-103-A1-M1-G4 |
| 25 | 54 | 43 | 64 | 59 | 197 | 271 | HG3_LIB5519-495-A1-M1-G5 |
| 25 | 54 | 43 | 64 | 59 | 48 | 122 | HG3_LIB5514-043-A1-P1-D11 |
| 25 | 54 | 43 | 64 | 62 | 197 | 271 | HG3_LIB5513-373-A1-M1-H2 |
| 25 | 54 | 43 | 64 | 58 | 197 | 271 | HG3_LIB5513-801-A1-P1-D5 |
| 25 | 54 | 43 | 64 | 58 | 197 | 271 | HG3_LIB5519-564-A1-P1-C9 |
| 25 | 54 | 43 | 64 | 59 | 35 | 109 | HG3_LIB5519-028-A1-P1-B10 |
| 25 | 54 | 43 | 64 | 58 | 197 | 271 | HG3_LIB5519-120-A1-P1-F12 |
| 25 | 54 | 43 | 64 | 64 | 197 | 271 | HG3_LIB5519-507-A1-M1-F3 |
| 25 | 54 | 43 | 64 | 59 | 197 | 271 | HG3_LIB5519-231-A1-M1-G2 |
| 25 | 54 | 43 | 64 | 59 | 197 | 271 | HG3_LIB5519-518-A1-M1-B2 |

TABLE 4-continued

| SCN mature miRNA | mature miRNA SEQ ID NO. | Nucleotide position of mature miRNA in pre-miRNA start | | Pre-miRNA SEQ ID NO | Nucleotide position of pre-miRNA in genomic locus start | | SCN genomic locus |
|---|---|---|---|---|---|---|---|
| | | start | end | | start | end | |
| 25 | 54 | 43 | 64 | 58 | 197 | 271 | HG3_LIB5513-224-A1-P1-E3 |
| 25 | 54 | 43 | 64 | 58 | 164 | 238 | HG3_LIB5513-691-A1-M1-G5 |
| 25 | 54 | 43 | 64 | 58 | 197 | 271 | HG3_LIB5519-295-A1-M1-G11 |
| 25 | 54 | 43 | 64 | 58 | 197 | 271 | HG3_LIB5513-052-A1-M1-F7 |
| 25 | 54 | 43 | 64 | 58 | 197 | 271 | HG3_LIB5519-450-A1-P1-F10 |
| 30 | 55 | 10 | 34 | 65 | 228 | 319 | HG3_1898.C5 |
| 31 | 56 | 65 | 87 | 66 | 696 | 793 | HG3_25240.C1 |
| 31 | 56 | 65 | 87 | 67 | 696 | 793 | HG3_23769.C1 |
| 31 | 56 | 65 | 87 | 66 | 690 | 787 | HG3_13335.C1 |
| 31 | 56 | 65 | 87 | 66 | 699 | 796 | HG3_21499.C1 |
| 31 | 56 | 64 | 86 | 68 | 151 | 247 | HG3_LIB5513-288-A1-M1-G12 |
| 31 | 56 | 64 | 86 | 68 | 49 | 145 | HG3_LIB5513-004-A1-M1-C6 |
| 31 | 56 | 10 | 32 | 69 | 133 | 230 | HG3_LIB5520-318-A1-P1-D7 |
| 31 | 56 | 64 | 86 | 68 | 140 | 236 | HG3_LIB5519-222-A1-P1-D9 |
| 31 | 56 | 64 | 86 | 68 | 174 | 270 | HG3_LIB5520-295-A1-M1-E8 |
| 31 | 56 | 64 | 86 | 68 | 138 | 234 | HG3_LIB5519-532-A1-M1-E2 |

Example 3

This example describes another non-limiting embodiment of a recombinant DNA construct that is transcribable in a plant cell to a recombinant miRNA precursor, preferably conferring on the plant resistance to an invertebrate pest. More particularly, this embodiment describes a recombinant DNA construct that includes sequence derived from multiple miRNA precursors, in this case nine invertebrate miRNA precursors that have homology to Western corn rootworm (WCR, *Diabrotica virgifera*) miRNA precursors.

From a library of small RNAs from Western corn rootworm was obtained nine clones with homology to known miRNAs; these putative WCR miRNAs are given in Table 5.

TABLE 5

| Small RNA ID | miRNA family | SEQ ID NO. | cloned WCR miRNA | Size (nt) |
|---|---|---|---|---|
| 2997059 | bta-miR-7 | 70 | TGGAAGACTAGTGATTTTGTTGTT | 24 |
| 1167198 | dme-miR-9a | 71 | TCTTTGGTTATCTAGCTGTATGA | 21 |
| 2999692 | dme-miR-14 | 72 | TCAGTCTTTTTCTCTCTCCTA | 22 |
| 3000551 | dme-miR-31a | 73 | GGCAAGATGTCGGCATAGCTG | 22 |
| 3000395 | sme-miR-71c | 74 | TGAAAGACATGGGTAGTGAGAT | 22 |
| 3000406 | aga-miR-92b | 75 | AATTGCACTTGTCCCGGCCTGC | 22 |
| 2998018 | dme-miR-275 | 76 | TCAGGTACCTGAAGTAGCGCGC | 22 |
| 2833118 | dme-miR-279 | 77 | TGACTAGATCCACACTCATTAA | 23 |
| 3007470 | dme-miR-305 | 78 | ATTGTACTTCATCAGGTGCTCT | 21 |

For each of the nine microRNAs, invertebrate pre-miRNA homologues were identified from MiRbase (eight from the fruit fly *Drosophila melanogaster* and one from the nematode *Caenorhabdites elegans*). The selected homologous pre-miRNA sequences (each including an additional 10 nucleotides upstream and downstream of the pre-miRNA, as indicated by the "+10" in the sequence name) were: "dme-mir-7+10" (GTCCTCCTGGGAGTGCATTCCGTATG-GAAGACTAGTGATTTTGTTGTTTGGTCTTTGGT AATAACAATAAATCCCTTGTCTTCT-TACGGCGTGCATTTGTGCTCTTCA, SEQ ID NO. 79), "dme-mir-9a+10" (TATACAGGGTGCTATGT-TGTCTTTGGTTATCTAGCTGTATGAGT-GATAAATAACGTCAT AAAGCTAGCTTACCGAAGT- TAATATTAGCGTCTGCCCAG, SEQ ID NO. 80), "dme-mir-14+10" (CTGCAACCTATGTGGGAGCGAGACGGG-GACTCACTGTGCTTATTAAATAGTCAGTCTT TTTCTCTCTCCTATACAAATTGCGG, SEQ ID NO. 81), "dme-mir-31a+10" (CGCTGACTGTTCCATTGAA-CAACTGACTAGATGCAGCATAGCGCTCT-TCAAAATCGCT TTTCAACGTCAGCTATGCCGA-CATCTTGCCAATTTACCAACGGAGTTGATATAC, SEQ ID NO. 82), "Cel-miR-71+10" (CACAGAGGTTGTCT-GCTCTGAACGATGAAAGACATGGGTAGT-GAGACGTCGGAGCCT CGTCGTATCACTATTCT-GTTTTTCGCCGTCGGGATCGTGACCTGGAAGCTGTA AACT, SEQ ID NO. 83), "dme-mir92a+10" (GC-CGAATATAAATATGAATTTCCCGTAG-GACGGGAAGGTGTCAACGTTTTGCATTTCG AATAAACATTGCACTTGTCCCGGC-CTATGGGCGGTTTGTAATAAACAACTAAAATCT, SEQ ID NO. 84), "dme-miR275+10" (TTCCCCCGACTG-TAAAGTCTCCTACCTTGCGCGCTAAT-CAGTGACCGGGGCTGGTTTTT TATATACAGTCAGG-TACCTGAAGTAGCGCGCGTGGTGGCAGACATATATC TCCATCTTC, SEQ ID NO. 85), "dme-miR279+10" (AGCTGGAATTGGAATTCATACTACT-GTTTTTAGTGGGTGGGGGTCCAGTGTTTCACATT GATTTTCTTAGTATTTGTGACTAGATC-CACACTCATTAATAACGGTAGTTCAATCATCA AG, SEQ ID NO. 86), and "dme-miR305+10" (AACTGTCTC-CCATGTCTATTGTACTTCATCAGGT-GCTCTGGTGTGTCTCGTAACCCGGC ACATGT-TGAAGTACACTCAATATGAGGCGATTTG, SEQ ID NO. 87).

The nine pre-miRNAs (including the extra "+10" nucleotides) were joined head-to-tail to yield a 951-nucleotide sequence, "miR-7+9+14+31+71+92+275+279+305" (GTC-CTCCTGGGAGTGCATTCCGTATGGAA-GACTAGTGATTTTGTTGTTTGGTCTTTGGT AATAA-CAATAAATCCCTTGTCTTCTTACGGCGTGCATTTGT GCTCTTCATATACAGGGT GCTATGTTGTCTTTGGT-TATCTAGCTGTATGAGT-GATAAATAACGTCATAAAGCTAGCT TACCGAAGT-TAATATTAGCGTCTGCCCAGCTGCAACCTATGTGGG AGCGAGACGGGGA CTCACTGTGCTTATTAAATAGT-CAGTCTTTTTCTCTCTCCTATACAAAT-TGCGGCGCTGA CTGTTCCATTGAACAACTGACTA-GATGCAGCATAGCGCTCTTCAAAATCGCTTTTCAAC GTCAGCTATGCCGACATCTTGCCAATT-TACCAACGGAGTTGATATACCACAGAGGTTGT CTGCTCTGAACGATGAAAGACATGGG-TAGTGAGACGTCGGAGCCTCGTCGTATCACTA TTCTGTTTTTCGCCGTCGGGATCGTGAC-CTGGAAGCTGTAAACTGCCGAATATAAATAT GAATTTCCCGTAGGACGGGAAGGTGT-CAACGTTTTGCATTTCGAATAAACATTGCACTT GTCCCGGCCTATGGGCGGTTTG-TAATAAACAACTAAAATCTTTC-CCCCGACTGTAAAGT CTCCTACCTTGCGCGCTAAT-CAGTGACCGGGGCTGGTTTTTTATATACAGTCAGGT ACC TGAAGTAGCGCGCGTGGTGGCAGA-CATATATCTCCATCTTCAGCTGGAATTGGAATTCA TACTACTGTTTTAGTGGGTGGGGGTC-CAGTGTTTCACATTGATTTTCTTAGTATTTGTG ACTAGATCCACACTCATTAATAACGG-TAGTTCAATCATCAAGAACTGTCTCCCATGTCT ATTGTACTTCATCAGGTGCTCTGGTGT-GTCTCGTAACCCGGCACATGTTGAAGTACACT CAATATG, SEQ ID NO. 88). This was synthesized by PCR using overlapping 50-mer oligonucleotides. The sequence was cloned into pCR4-TOPO vector (Invitrogen), yielding plasmid pMON97886, from which T7 polymerase was used to generate RNA.

The resulting RNA corresponding to SEQ ID NO. 88 is tested in a Western corn rootworm (WCR, *Diabrotica virgifera*) larval diet bioassay (described in U.S. Patent Application Publication US 2006/0021087 A1, incorporated by reference), and mortality and stunting against WCR larvae is measured.

Example 4

This example describes another non-limiting embodiment of a recombinant DNA construct that is transcribable in a plant cell to a recombinant miRNA precursor, preferably conferring on the plant resistance to an invertebrate pest. More particularly, this embodiment describes a recombinant DNA construct that includes artificial miRNA precursor sequences derived from soybean cyst nematode (*Heterodera glycine*, SCN) miRNA sequences engineered to suppress an invertebrate target gene.

When expressed as dsRNA in soybean, major sperm protein1 (MSP1) has been reported to cause significant mortality in *H. glycines*; see Steeves et al. (2006) *Funct. Plant Biol.*, 33:991-999. A 21-nucleotide sequence, TCTTGAGACT-GTCCTGTATTA (SEQ ID NO. 89), from *H. glycines* MSP1 (SEQ ID NO. 90) was selected as the target sequence, based on functional asymmetry and efficacy predictors as described by Reynolds et al. (2004) *Nature Biotechnol.*, 22:326-330 and Khvorova et al. (2003) *Cell*, 115:209-216. The "SCN15" pre-miRNA sequence (SEQ ID NO. 57) that produces the "SCN15" mature miRNA (SEQ ID NO. 53) (see Example 2) was modified by replacing the nucleotides of the "SCN15" mature miRNA with the engineered mature miRNA "SCN15-miRMSP1" (SEQ ID NO. 91), and the complementary region of the foldback was changed to maintain the original paired and unpaired bases, yielding the engineered pre-miRNA sequence "SCN15-MIRMSP1" (SEQ ID NO. 92); see FIG. 6A. The synthetic pre-miRNA "SCN15-MIRMSP1" (SEQ ID NO. 92) is cloned into a binary expression vector with a constitutive or root-specific promoter, transformed into soybean, and assayed for efficacy at protecting against SCN, e.g., with the bioassay described by Steeves et al. (2006) *Funct. Plant Biol.*, 33:991-999).

Example 5

This example describes another non-limiting embodiment of a recombinant DNA construct that is transcribable in a plant cell to a recombinant miRNA precursor, preferably conferring on the plant resistance to an invertebrate pest. More particularly, this embodiment describes a recombinant DNA construct that includes artificial miRNA precursor sequences derived from soybean cyst nematode (*Heterodera glycine*, SCN) miRNA sequences engineered to suppress an invertebrate target gene.

A 22-nucleotide sequence, TGGTGCGTGGACTAGTG-GTGAG (SEQ ID NO. 93), from *H. glycines* cgh-1 (SEQ ID NO. 94) was selected as the target sequence, based on functional asymmetry and efficacy predictors as described by Reynolds et al (2004) *Nature Biotechnol.*, 22:326-330 and Khvorova et al. (2003) *Cell*, 115:209-216. An "SCN25" pre-miRNA sequence (SEQ ID NO. 58) that produces the "SCN25" mature miRNA (SEQ ID NO. 54) (see Example 2) was modified by replacing the nucleotides of the "SCN25" mature miRNA with the engineered mature miRNA "SCN25- miRcgh1" (SEQ ID NO. 95), and the complementary region of the foldback was changed to maintain the original paired and unpaired bases, yielding the engineered pre-miRNA sequence "SCN25-MIRcgh1" (SEQ ID NO. 96); see FIG. 6B. The synthetic pre-miRNA "SCN25-MIRcgh1" (SEQ ID NO. 96) is cloned into a binary expression vector with a constitutive or root-specific promoter, transformed into soybean, and assayed for efficacy at protecting against SCN, e.g., with the bioassay described by Steeves et al. (2006) *Funct. Plant Biol.*, 33:991-999).

Example 6

In many embodiments of this invention, the recombinant DNA construct further includes one or more elements selected from: (a) a promoter functional in a plant cell; (b) a transgene transcription unit; (c) a gene suppression element; and (d) a transcription regulatory/transcript stabilizing element. This example further illustrates non-limiting embodiments of gene suppression elements. Gene suppression elements can include, but are not limited to, the invertebrate mature miRNAs and miRNA precursors that are aspects of this invention.

FIG. 7A schematically depicts non-limiting examples of recombinant DNA constructs that illustrate arrangement of components of the construct. In these non-limiting examples, the constructs include at least one first gene suppression element ("GSE" or "GSE1") for suppressing at least one first target gene, wherein the first gene suppression element is embedded in an intron flanked on one or on both sides by non-protein-coding DNA. These constructs utilize an intron (in many embodiments, an intron derived from a 5' untranslated region or an expression-enhancing intron is preferred) to deliver a gene suppression element without requiring the presence of any protein-coding exons (coding sequence). The constructs can optionally include at least one second gene suppression element ("GSE2") for suppressing at least one second target gene, at least one gene expression element ("GEE") for expressing at least one gene of interest (which can be coding or non-coding sequence or both), or both. In embodiments containing an optional gene expression element, the gene expression element can be located outside of (e.g., adjacent to) the intron. In some embodiments, the intron containing the first gene suppression element is 3' to a terminator.

To more clearly differentiate recombinant DNA constructs of the invention (containing at least one gene suppression element embedded within a single intron flanked on one or on both sides by non-protein-coding DNA) from the prior art, FIG. 7B schematically depicts examples of prior art recombinant DNA constructs. These constructs can contain a gene suppression element that is located adjacent to an intron flanked by protein-coding sequence, or between two discrete introns (wherein the gene suppression element is not embedded in either of the two discrete introns), or can include a gene expression element including a gene suppression element embedded within an intron which is flanked by multiple exons (e.g., exons including the coding sequence of a protein).

FIG. 8 depicts various non-limiting examples of gene suppression elements useful in the recombinant DNA constructs of the invention. Where drawn as a single strand (FIGS. 8A through 8E), these are conventionally depicted in 5' to 3' (left to right) transcriptional direction; the arrows indicate anti-sense sequence (arrowhead pointing to the left), or sense sequence (arrowhead pointing to the right). These gene suppression elements can include: DNA that includes at least one anti-sense DNA segment that is anti-sense to at least one segment of at least one first target gene, or DNA that includes multiple copies of at least one anti-sense DNA segment that is anti-sense to at least one segment of at least one first target gene (FIG. 8A); DNA that includes at least one sense DNA segment that is at least one segment of at least one first target gene, or DNA that includes multiple copies of at least one sense DNA segment that is at least one segment of at least one first target gene (FIG. 8B); DNA that transcribes to RNA for suppressing at least one first target gene by forming double-stranded RNA and includes at least one anti-sense DNA segment that is anti-sense to at least one segment of at least one first target gene and at least one sense DNA segment that is at least one segment of at least one first target gene (FIG. 8C); DNA that transcribes to RNA for suppressing at least one first target gene by forming a single double-stranded RNA and includes multiple serial anti-sense DNA segments that are anti-sense to at least one segment of at least one first target gene and multiple serial sense DNA segments that are at least one segment of at least one first target gene (FIG. 8D); DNA that transcribes to RNA for suppressing at least one first target gene by forming multiple double strands of RNA and includes multiple anti-sense DNA segments that are anti-sense to at least one segment of at least one first target gene and multiple sense DNA segments that are at least one segment of at least one first target gene, and wherein the multiple anti-sense DNA segments and the multiple sense DNA segments are arranged in a series of inverted repeats (FIG. 8E); and DNA that includes nucleotides derived from a miRNA (including, but not limited to, nucleotides derived from the invertebrate mature miRNAs and miRNA precursors of this invention), or DNA that includes nucleotides of a siRNA (FIG. 8F).

FIG. 8F depicts various non-limiting arrangements of double-stranded RNA that can be transcribed from embodiments of the gene suppression elements useful in the recombinant DNA constructs of the invention. When such double-stranded RNA is formed, it can suppress one or more target genes, and can form a single double-stranded RNA or multiple double strands of RNA, or a single double-stranded RNA "stem" or multiple "stems". Where multiple double-stranded RNA "stems" are formed, they can be arranged in "hammerheads" or "cloverleaf" arrangements. In some embodiments, the double-stranded stems can form a "pseudoknot" arrangement (e.g., where spacer or loop RNA of one double-stranded stem forms part of a second double-stranded stem); see, for example, depictions of pseudoknot architectures in Staple and Butcher (2005) *PLoS Biol.*, 3(6): e213. Spacer DNA (located between or adjacent to dsRNA regions) is optional but commonly included and generally includes DNA that does not correspond to the target gene (although in some embodiments can include sense or anti-sense DNA of the target gene). Spacer DNA can include sequence that transcribes to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A non-natural plant having resistance to an invertebrate pest that ingests RNA from said plant, wherein
said non-natural plant comprises a transgenic plant cell having in its genome a recombinant DNA construct that comprises a promoter functional in a plant cell and that is transcribed in said transgenic plant cell to a recombinant miRNA precursor; and
said recombinant miRNA precursor comprises a single strand of RNA that folds into a secondary structure of a miRNA precursor identified from an invertebrate genome and that comprises at least one stem-loop that is processed to a mature miRNA; and
said mature miRNA suppresses expression of at least one target gene of said invertebrate pest or of a symbiont associated with said invertebrate pest, thereby conferring on said non-natural plant resistance to said invertebrate pest.

2. The non-natural plant of claim 1, wherein said at least one stem-loop that is processed to a mature miRNA comprises a stem region and a loop region, wherein
said stem region comprises a first segment and a second segment,
said first segment comprises at least 19 contiguous nucleotides for silencing a messenger RNA encoding said target gene,
said second segment comprises at least 19 contiguous nucleotides,
said loop region is located between said first and second segments, and
said first and second segments hybridize to form partially double stranded RNA, wherein at least one nucleotide of said first segment is unpaired.

3. The non-natural plant of claim 2, wherein said at least 19 contiguous nucleotides for silencing a messenger RNA have at least 70% complementarity to a segment of equivalent length in said messenger RNA.

4. The non-natural plant of claim 3, wherein said loop region comprises a native loop sequence of said miRNA precursor identified from an invertebrate genome.

5. The non-natural plant of claim 1, wherein said invertebrate pest is at least one selected from the group consisting of insects, arachnids, nematodes, molluscs, and annelids.

6. The non-natural plant of claim 1, wherein said at least one target gene is (a) a single target gene, or (b) multiple target genes.

7. The non-natural plant of claim 1, wherein said at least one target gene is an endogenous target of an invertebrate miRNA natively expressed from said miRNA precursor identified from an invertebrate genome.

8. The non-natural plant of claim 1, wherein said at least one target gene is other than an endogenous target of an invertebrate miRNA natively expressed from said miRNA precursor identified from an invertebrate genome.

9. The non-natural plant of claim 1, wherein said at least one target gene is a target gene of a symbiont associated with said invertebrate pest.

10. The non-natural plant of claim 1, wherein
(a) said non-natural plant is maize and said invertebrate pest is a *Diabrotica* species;
(b) said non-natural plant is soybean and said invertebrate pest is a soybean cyst nematode;
(c) said non-natural plant is a grape and said invertebrate pest is a grape phylloxera or a glassy-winged sharpshooter (*Homalodisca coagulata*); or
(d) said non-natural plant is an apple and said invertebrate pest is a woolly apple aphid.

11. The non-natural plant of claim 1, wherein said recombinant DNA construct further comprises one or more elements selected from:
(a) a transgene transcription unit;
(b) a gene suppression element; and
(c) a transcription regulatory/transcript stabilizing element.

12. The non-natural plant of claim 1, wherein said non-natural plant is a transgenic plant.

13. The non-natural plant of claim 1, wherein said non-natural plant further comprises non-transgenic tissue.

14. The non-natural plant of claim 13, wherein said plant comprises a non-transgenic scion and a transgenic rootstock comprising said transgenic plant cell.

15. A non-natural transgenic plant cell having in its genome a recombinant DNA construct that comprises a promoter functional in a plant cell and that is transcribed in said non-natural transgenic plant cell to a recombinant miRNA precursor, wherein said recombinant miRNA precursor comprises a single strand of RNA that folds into a secondary structure of an invertebrate a miRNA precursor identified from an invertebrate genome and that comprises at least one stem-loop that is processed to a mature miRNA, and wherein said mature miRNA suppresses expression of at least one target gene of an invertebrate or of a symbiont associated with said invertebrate.

16. A non-natural transgenic plant grown from the non-natural transgenic plant cell of claim 15.

17. Non-natural transgenic seed produced by the non-natural transgenic plant of claim 16 and having in its genome said recombinant DNA construct.

18. A method of suppressing at least one target gene of an invertebrate pest of a plant, comprising providing a plant comprising the non-natural transgenic plant cell of claim 15, wherein
said invertebrate is said invertebrate pest,
said recombinant DNA construct is transcribed in said non-natural transgenic plant cell to said recombinant miRNA precursor, and
when said invertebrate pest ingests said recombinant miRNA precursor, said at least one target gene is suppressed.

19. The non-natural plant of claim 1, wherein said recombinant miRNA precursor is encoded by DNA having a sequence selected from the group consisting of SEQ ID NOs: 1-10, 28-35, 44-46, and 79-88, or has RNA sequence selected from the group consisting of SEQ ID NOs:11-18, 36-43, 57-69, 92, and 96.

20. The non-natural transgenic plant cell of claim 15, wherein said recombinant miRNA precursor is encoded by DNA having a sequence selected from the group consisting of SEQ ID NOs:1-10, 28-35, 44-46, and 79-88, or has RNA sequence selected from the group consisting of SEQ ID NOs: 11-18, 36-43, 57-69, 92, and 96.

21. The method of claim 18, wherein said recombinant miRNA precursor is encoded by DNA having a sequence selected from the group consisting of SEQ ID NOs:1-10, 28-35, 44-46, and 79-88, or has RNA sequence selected from the group consisting of SEQ ID NOs:11-18, 36-43, 57-69, 92, and 96.

* * * * *

UNITED STATES PATENT AND TRADEMARK OFFICE
CERTIFICATE OF CORRECTION

| | | |
|---|---|---|
| PATENT NO. | : 8,410,334 B2 | Page 1 of 1 |
| APPLICATION NO. | : 12/033178 | |
| DATED | : April 2, 2013 | |
| INVENTOR(S) | : Edwards Allen et al. | |

It is certified that error appears in the above-identified patent and that said Letters Patent is hereby corrected as shown below:

In the Claims claim 15, column 82, line 23, delete "an invertabrate"
claim 19, column 82, line 49, add --an-- after the word has and before the word RNA
claim 20, column 82, line 56, add --an-- after the word has and before the word RNA
claim 21, column 82, line 62, add --an-- after the word has and before the word RNA Signed and Sealed this
Twenty-eighth Day of January, 2014

Michelle K. Lee
*Deputy Director of the United States Patent and Trademark Office*

```
                              SEQUENCE LISTING

<160> NUMBER OF SEQ ID NOS: 96

<210> SEQ ID NO 1
<211> LENGTH: 1502
<212> TYPE: DNA
<213> ORGANISM: Drosophila melanogaster

<400> SEQUENCE: 1
aaaattttca ctaaggtcgt cgcgatccgg gacgcgaatt cgcggaacag ccccgaccct      60
ttcaggtaac aacgcccgcc acccacaggt aggtgtttat aggacaagaa agtgggtata     120
aaagatctag ccgctggcaa ggaagtcatc agttaccaac gcatcttcaa agtgtaagga     180
tcccgcagtg agaagcgaag tcttaaagtt tggaatagca attatacgac aaaccttgtt     240
cggttttgcc aatttccaag ccagcactgg gtaaagtttg tcctataatc ccgaaacgac     300
gaccagctaa ttgtgagcca cctaaggtcc cgatcctggg atgcatcttg tgcagttatg     360
tttcaatctc acatcactgg gcaaagtgtg tctcaagatc ctggccacat cgtcgcaact     420
tcaaatcaat taaatcaaaa aatcaagagt aagtgatatt gggcactcca gttttaaaat     480
tgaatggcga atgtcggtat ggtctctttt tcaaagaaag gtttcgatta agcgaagtga     540
ctagaccgaa cactcgtgct ataattttaa aatattcaac atgctcagta aagttgcgag     600
tgaaaattaa aatattatgg agcggttgca attagtttct ttggtcgtcc agccttaggt     660 gattttccg gtcataaagc tagacaacca ttgaagttcg ttgtggcatt agcagcacca     720
cgagtcaaga aattatgtta agtgatcccc aaattcatcg ggccattcgc taaaaggaac     780
gatcgttgtg atatgagttg tttcctaaca tatcacagtg attttccttt ataacgcatg     840
tttaaagtcc acaactcatc aaggaaaatg aaagtcaaag ttggcagctt acttaaactt     900
aatcacagcc tttaatgtag agggaatagt tgctgtgctg taagttaata taccatatct     960
atatcacagt ggctgttctt tttgtaccta aagtgcctaa catcattatt taatttttt    1020 ttttttggc acacgaataa ccatgccgtt tttaacccaa gggaacttct gctgctgata    1080
tattattgaa aaactactat atcacagtgg ctgttctttt tggttgcacg gccaattcca    1140
acgatttgtc atttgtggca cgcatttgtg tcacctcagt gcgaaaattg aaaattgtac    1200
aaaaagaagg gaacggttgc tgatgatgta gtttgaaact ctcacaattt atatcacagt    1260
ggctgttctt ttttgtttgg caatcgatct acgttcagtg gtttgccagg acatgaaaca    1320
gaaatatttt ccgtcaacag acttctgatt gcacaaattc ctcaagcttt gaacatttgg    1380
gaaaaactga tgagacgttg gttttctagc ttgtgcatca attcgtcatt tgtctgcagt    1440
tttgtcaatc tttaattgca ctttacaatt cattgctttt tgttcaatca tttttgggtg    1500
gt                                                                   1502

<210> SEQ ID NO 2
<211> LENGTH: 1059
<212> TYPE: DNA
<213> ORGANISM: Drosophila melanogaster

<400> SEQUENCE: 2
attatacgac aaaccttgtt cggttttgcc aatttccaag ccagcactgg gtaaagtttg      60
tcctataatc ccgaaacgac gaccagctaa ttgtgagcca cctaaggtcc cgatcctggg     120
```

```
atgcatcttg tgcagttatg tttcaatctc acatcactgg gcaaagtgtg tctcaagatc    180
ctggccacat cgtcgcaact tcaaatcaat taaatcaaaa aatcaagagt aagtgatatt    240
gggcactcca gttttaaaat tgaatggcga atgtcggtat ggtctctttt tcaaagaaag    300
gtttcgatta agcgaagtga ctagaccgaa cactcgtgct ataattttaa aatattcaac    360
atgctcagta aagttgcgag tgaaaattaa aatattatgg agcggttgca attagtttct    420
ttggtcgtcc agccttaggt gattttccg gtcataaagc tagacaacca ttgaagttcg     480
ttgtggcatt agcagcacca cgagtcaaga aattatgtta agtgatcccc aaattcatcg    540
ggccattcgc taaaaggaac gatcgttgtg atatgagttg tttcctaaca tatcacagtg    600 atttteettt ataacgcatg tttaaagtcc acaactcatc aaggaaaatg aaagtcaaag    660
ttggcagctt acttaaactt aatcacagcc tttaatgtag agggaatagt tgctgtgctg    720
taagttaata taccatatct atatcacagt ggctgttctt tttgtaccta aagtgcctaa    780
catcattatt taattttttt tttttttggc acacgaataa ccatgccgtt tttaacccaa    840
gggaacttct gctgctgata tattattgaa aaactactat atcacagtgg ctgttctttt    900
tggttgcacg gccaattcca acgatttgtc atttgtggca cgcatttgtg tcacctcagt    960
gcgaaaattg aaaattgtac aaaaagaagg gaacggttgc tgatgatgta gtttgaaact   1020
ctcacaattt atatcacagt ggctgttctt ttttgtttg                          1059

<210> SEQ ID NO 3
<211> LENGTH: 69
<212> TYPE: DNA
<213> ORGANISM: Drosophila melanogaster

<400> SEQUENCE: 3
attatacgac aaaccttgtt cggttttgcc aatttccaag ccagcactgg gtaaagtttg     60
tcctataat                                                            69

<210> SEQ ID NO 4
<211> LENGTH: 69
<212> TYPE: DNA
<213> ORGANISM: Drosophila melanogaster

<400> SEQUENCE: 4
gatcctggga tgcatcttgt gcagttatgt ttcaatctca catcactggg caaagtgtgt     60
ctcaagatc                                                            69

<210> SEQ ID NO 5
<211> LENGTH: 100
<212> TYPE: DNA
<213> ORGANISM: Drosophila melanogaster

<400> SEQUENCE: 5
ttaaaattga atggcgaatg tcggtatggt ctcttttca aagaaaggtt tcgattaagc      60
gaagtgacta gaccgaacac tcgtgctata attttaaaat                          100

<210> SEQ ID NO 6
<211> LENGTH: 81
<212> TYPE: DNA
<213> ORGANISM: Drosophila melanogaster

<400> SEQUENCE: 6
ttgcaattag tttctttggt cgtccagcct taggtgattt ttccggtcat aaagctagac     60
aaccattgaa gttcgttgtg g                                              81
```

```
<210> SEQ ID NO 7
<211> LENGTH: 69
<212> TYPE: DNA
<213> ORGANISM: Drosophila melanogaster

<400> SEQUENCE: 7
gctaaaagga acgatcgttg tgatatgagt tgtttcctaa catatcacag tgattttcct    60
ttataacgc                                                            69

<210> SEQ ID NO 8
<211> LENGTH: 82
<212> TYPE: DNA
<213> ORGANISM: Drosophila melanogaster

<400> SEQUENCE: 8
tttaatgtag agggaatagt tgctgtgctg taagttaata taccatatct atatcacagt    60
ggctgttctt tttgtaccta aa                                             82

<210> SEQ ID NO 9
<211> LENGTH: 74
<212> TYPE: DNA
<213> ORGANISM: Drosophila melanogaster

<400> SEQUENCE: 9
taacccaagg gaacttctgc tgctgatata ttattgaaaa actactatat cacagtggct    60 gttcttttg gttg                                                       74

<210> SEQ ID NO 10
<211> LENGTH: 80
<212> TYPE: DNA
<213> ORGANISM: Drosophila melanogaster

<400> SEQUENCE: 10
caaaaagaag ggaacggttg ctgatgatgt agtttgaaac tctcacaatt tatatcacag    60
tggctgttct tttttgtttg                                                80

<210> SEQ ID NO 11
<211> LENGTH: 69
<212> TYPE: RNA
<213> ORGANISM: Drosophila melanogaster

<400> SEQUENCE: 11
auuauacgac aaaccuuguu cgguuuugcc aauuccaag ccagcacugg guaaaguuug     60
uccuauaau                                                            69

<210> SEQ ID NO 12
<211> LENGTH: 69
<212> TYPE: RNA
<213> ORGANISM: Drosophila melanogaster

<400> SEQUENCE: 12
gauccuggga ugcaucuugu gcaguuaugu uucaaucuca caucacuggg caaagugugu    60
cucaagauc                                                            69

<210> SEQ ID NO 13
<211> LENGTH: 100
<212> TYPE: RNA
<213> ORGANISM: Drosophila melanogaster

<400> SEQUENCE: 13
```

```
uuaaaauuga auggcgaaug ucgguauggu cucuuuuuca aagaaagguu ucgauuaagc     60
gaagugacua gaccgaacac ucgugcuaua auuuuaaaau                         100

<210> SEQ ID NO 14
<211> LENGTH: 81
<212> TYPE: RNA
<213> ORGANISM: Drosophila melanogaster

<400> SEQUENCE: 14
uugcaauuag uuucuuuggu cguccagccu uaggugauuu uuccggucau aaagcuagac     60
aaccauugaa guucguugug g                                              81

<210> SEQ ID NO 15
<211> LENGTH: 69
<212> TYPE: RNA
<213> ORGANISM: Drosophila melanogaster

<400> SEQUENCE: 15
gcuaaaagga acgaucguug ugauaugagu uguuccuaa cauaucacag ugauuuuccu      60
uuauaacgc                                                            69

<210> SEQ ID NO 16
<211> LENGTH: 82
<212> TYPE: RNA
<213> ORGANISM: Drosophila melanogaster

<400> SEQUENCE: 16
uuuaauguag agggaauagu ugcugugcug uaaguuaaua uaccauaucu auaucacagu     60
ggcuguucuu uuuguaccua aa                                             82

<210> SEQ ID NO 17
<211> LENGTH: 74
<212> TYPE: RNA
<213> ORGANISM: Drosophila melanogaster

<400> SEQUENCE: 17
uaacccaagg gaacuucugc ugcugauaua uuauugaaaa acuacuauau cacaguggcu     60
guucuuuuug guug                                                      74

<210> SEQ ID NO 18
<211> LENGTH: 80
<212> TYPE: RNA
<213> ORGANISM: Drosophila melanogaster

<400> SEQUENCE: 18
caaaaagaag ggaacgguug cugaugaugu aguuugaaac ucucacaauu uauaucacag     60
uggcuguucu uuuuuguuug                                                80

<210> SEQ ID NO 19
<211> LENGTH: 2891
<212> TYPE: DNA
<213> ORGANISM: Diabrotica virgifera

<400> SEQUENCE: 19
cgcacgcctg caccgtaccg gaaactcgtc cataatcgcg atagttgagt gggtgaggtt     60
ccaagagaaa cataacatcc atccacaaat atgtcgaaag taaggatcgg agatgaagag    120
aaggaagggc agtatggtta tgtccatgct gtctcaggtc cagtcgttac tgctgagaaa    180
atgtctggtt ctgctatgta cgaactggta cgtgtcggat actatgagct ggtaggagaa    240
```

```
atcattagat tggaaggtga catggctact attcaggtat acgaagaaac atcaggtgta      300
actgttggtg atccagtatt aagaactggt aaaccacttt cagtagaact tggacctggt      360
attatgggtt ccatttttga tggtatccaa cgtccattga agacatttg tgacgctact       420 gatagtattt acatccccaa gggtattaac gtaccttctt tatcgagaac agcaaaatgg      480
gacttcaacc caatcaacat caagttggga tctcacttaa ctggaggtga tatatatggt      540
ctagttcatg aaaacaccct tgtcaaacac aaaatgattc tgcctcctag agctaagggt      600
actgtaacct acattgcaga accaggaaac tacactgttg atgaagtagt attggaaact      660
gaatttgatg gtgatcgtac caaatatact atgttgcaag tatggcctgt acgtcaagca      720
aggccagtca gtgaaaaatt acctgccaac catcctctgc ttacaggaca gcgtgtactt      780
gatgctcttt tcccatgtgt acagggtggt actactgcca ttcccggagc tttcggttgt      840
ggaaaaactg taatttcaca atctctttcc aaatattcca actctgatgt cattatctac      900
gtcggttgcg gagaaagagg taacgaaatg tctgaagtat tgagagattt ccctgaattg      960
actgttgaaa ttgacgggca cactgaatct attatgaaac gtaccgcatt ggtcgccaac     1020
acatctaaca tgcctgtagc tgctcgtgaa gcttctatct atactggtat tactcttttct    1080 gaatacttcc gtgatatggg ttacaacgta tctatgatgg ctgactcgac atcacgttgg     1140
gccgaagctt tgagagaaat ttcaggtcgt ttggctgaaa tgcctgccga ttccggttat     1200
ccggcttact taggtgcccg tttggcttcc ttctacgaac gtgctggtcg cgttaaatgt     1260
ttaggtaatc cagacagaga aggatccgtt tcaattgtag gagccgtatc acctcctggt     1320
ggtgatttct cagatcctgt taccactgct actcttggta ttgtacaggt gttctggggt     1380
ttggacaaga aacttgccca acgtaagcac ttcccttcag tagactggct tggatcatat     1440
tccaaatatt taagagcatt ggacgacttt tatgacaaaa acttccaaga gtttattcct     1500
cttagaacca agttaaggga aattcttcag gaagaagatg atctagccga aattgtgcag     1560
ctggtaggta agcatctct ggcagaaacg gacaaaatca ccttggaaat tgccaggctt     1620
cttaaagaag atttcttgca acaaaactca tactcttctt atgacagatt ctgtccattc     1680
tataaaactg tcggtatgtt gagaaacatg atcggtttgt acgacatggc gagacacgct     1740
gtagaatcaa ccgcacaatc agaaaataag atcacttgga acgtaataag agattcaatg     1800
agtggaattt tatatcaact tagcagtatg aaatttaagg atcccgtaaa agatggtgaa     1860
gctaaaatca aggcagattt tgatcaatta tatgaagata ttcagcaggc cttcagaaac     1920
ttagaagatt aaatctttt aaggaaattt tcctattttg ttcatcagtg taagtttaaa      1980
aatatagcga tatttatcaa aaagaataat aaggcctcta tccctcactt ctgtgaatat     2040
taatatggcc gtactaaaga tagtaactaa agataggttt tctcttttt gatattatcc     2100 tgtacaaaat aaattatgta aattgttgaa tatgtgtata gttttttgg gtgagggtac      2160 agtgcttatt aaatactttt taaacatttt tcccgccatt ccaattacta ttaagttttt     2220
tcgttttaat acttttttaa atatacaggt gcttaatatc gtttatattt tcagtattac     2280
ttggttttct tcatgtaaat tgtttttaaat ttttcttttta ccctttttaat cttgtatatt  2340 acattaccca attaaagtta attgtacaga ttaagataaa cgagtatctt ataacatcta     2400
ttagattgtt agaatcaata aatgtagtgt aattgttctg ttttgaacaa ataaatgcat     2460
cattattgtt gaaaaaaaaa aaaaagggc ggccgctcgc gatctagaac tagtttttttt    2520 ttttttacca taaaaattta atattttaaa tactccatca cataaacatc ataaaaacat     2580
aaaatcactc attaagacga tgagacaagc tgaacttcct ttccagtttt tttgataatc     2640
```

```
tccaagacat cattagcagg caaagttgat ttcactttaa cactctgact ttccagactt    2700
atagaaactt cttccacacc ttttccaacg tgtttattta gagctctttc cacagcacca    2760
ctgcatcctc cacaggtcat ttttacgttg aattcgtgta tttgggacat ctttgatttg    2820
ttgttgatcg aataagtgat gttttagaca gcacggacgc agatgggtcg gaccccgggg    2880
aattcccggg a                                                        2891
```

```
<210> SEQ ID NO 20
<211> LENGTH: 19
<212> TYPE: DNA
<213> ORGANISM: Diabrotica virgifera

<400> SEQUENCE: 20
gactggcttg gatcatatt                                                19

<210> SEQ ID NO 21
<211> LENGTH: 19
<212> TYPE: DNA
<213> ORGANISM: Diabrotica virgifera

<400> SEQUENCE: 21
gagcattgga cgacttta                                                 19

<210> SEQ ID NO 22
<211> LENGTH: 19
<212> TYPE: DNA
<213> ORGANISM: Diabrotica virgifera

<400> SEQUENCE: 22
tgtgcagctg gtaggtaaa                                                19

<210> SEQ ID NO 23
<211> LENGTH: 19
<212> TYPE: DNA
<213> ORGANISM: Diabrotica virgifera

<400> SEQUENCE: 23
tggcagaaac ggacaaaat                                                19

<210> SEQ ID NO 24
<211> LENGTH: 19
<212> TYPE: DNA
<213> ORGANISM: Diabrotica virgifera

<400> SEQUENCE: 24
tgccaggctt cttaaagaa                                                19

<210> SEQ ID NO 25
<211> LENGTH: 19
<212> TYPE: DNA
<213> ORGANISM: Diabrotica virgifera

<400> SEQUENCE: 25
gcaggccttc agaaactta                                                19

<210> SEQ ID NO 26
<211> LENGTH: 19
<212> TYPE: DNA
<213> ORGANISM: Diabrotica virgifera

<400> SEQUENCE: 26
tggccgtact aaagatagt                                                19
```

```
<210> SEQ ID NO 27
<211> LENGTH: 19
<212> TYPE: DNA
<213> ORGANISM: Diabrotica virgifera

<400> SEQUENCE: 27
gagggtacag tgcttatta                                                    19

<210> SEQ ID NO 28
<211> LENGTH: 69
<212> TYPE: DNA
<213> ORGANISM: artificial sequence
<220> FEATURE:
<223> OTHER INFORMATION: synthetic construct

<400> SEQUENCE: 28
attagtcgac tggcctggat cataattgcc aatttccaag ccaaatatga tccaagccag        60
tctactaat                                                               69

<210> SEQ ID NO 29
<211> LENGTH: 69
<212> TYPE: DNA
<213> ORGANISM: artificial sequence
<220> FEATURE:
<223> OTHER INFORMATION: synthetic construct

<400> SEQUENCE: 29
gatcctaaga gcattcgacg tctttcatgt ttcaatctca cataaaagtc gtccaatgct        60
cttaagatc                                                               69

<210> SEQ ID NO 30
<211> LENGTH: 97
<212> TYPE: DNA
<213> ORGANISM: artificial sequence
<220> FEATURE:
<223> OTHER INFORMATION: synthetic construct

<400> SEQUENCE: 30
ttaaaattga acgtgtggag cggtaagtaa atcttttca aagaaaggtt tcgattaagc         60
gaagttttac ctaccagctg cacaattata attttaa                                97

<210> SEQ ID NO 31
<211> LENGTH: 82
<212> TYPE: DNA
<213> ORGANISM: artificial sequence
<220> FEATURE:
<223> OTHER INFORMATION: synthetic construct

<400> SEQUENCE: 31
ttgcaattag ttctacggca caaaaggact cttatgattt ttccggtcat tttgtccgtt        60
tctgccagag agttcgttgt gg                                                82

<210> SEQ ID NO 32
<211> LENGTH: 67
<212> TYPE: DNA
<213> ORGANISM: artificial sequence
<220> FEATURE:
<223> OTHER INFORMATION: synthetic construct

<400> SEQUENCE: 32
gctattcttt aagaagcctg gcaattagtt gtttcctata attgccaggc ttctaaagaa        60
ataacgc                                                                 67
```

<210> SEQ ID NO 33
<211> LENGTH: 82
<212> TYPE: DNA
<213> ORGANISM: artificial sequence
<220> FEATURE:
<223> OTHER INFORMATION: synthetic construct

<400> SEQUENCE: 33
tttaatgttc agcaggcctt tagaaaccta agttaata taccatatct ataagtttct    60
gaaggcctgc tgagtaccta aa                                          82

<210> SEQ ID NO 34
<211> LENGTH: 75
<212> TYPE: DNA
<213> ORGANISM: artificial sequence
<220> FEATURE:
<223> OTHER INFORMATION: synthetic construct

<400> SEQUENCE: 34
taacccatat ggcctcacta aagatagtta ttattgaaaa actactaact atctttagta    60
cggccatatt ggttg                                                    75

<210> SEQ ID NO 35
<211> LENGTH: 80
<212> TYPE: DNA
<213> ORGANISM: artificial sequence
<220> FEATURE:
<223> OTHER INFORMATION: synthetic construct

<400> SEQUENCE: 35 caaaaggtg agggtacagt gctatattat agtttgaaac tctcacaatt tataataagc    60
actgtaccct cacctgtttg                                              80

<210> SEQ ID NO 36
<211> LENGTH: 69
<212> TYPE: RNA
<213> ORGANISM: artificial sequence
<220> FEATURE:
<223> OTHER INFORMATION: synthetic construct

<400> SEQUENCE: 36
auuagucgac uggccuggau cauaauugcc aauuccaag ccaauauga uccaagccag      60 ucuacuaau                                                           69

<210> SEQ ID NO 37
<211> LENGTH: 69
<212> TYPE: RNA
<213> ORGANISM: artificial sequence
<220> FEATURE:
<223> OTHER INFORMATION: synthetic construct

<400> SEQUENCE: 37
gauccuaaga gcauucgacg ucuuucaugu uucaaucuca cauaaaaguc guccaaugcu    60
cuuaagauc                                                           69

<210> SEQ ID NO 38
<211> LENGTH: 97
<212> TYPE: RNA
<213> ORGANISM: artificial sequence
<220> FEATURE:
<223> OTHER INFORMATION: synthetic construct

<400> SEQUENCE: 38

```
uuaaaauuga acguguggag cgguaaguaa aucuuuuuca aagaaagguu ucgauuaagc      60
gaaguuuuac cuaccagcug cacaauuaua auuuuaa                              97

<210> SEQ ID NO 39
<211> LENGTH: 82
<212> TYPE: RNA
<213> ORGANISM: artificial sequence
<220> FEATURE:
<223> OTHER INFORMATION: synthetic construct

<400> SEQUENCE: 39
uugcaauuag uucuacggca caaaaggacu cuuaugauuu uccggucau uuguccguu       60 ucugccagag aguucguugu gg                                              82

<210> SEQ ID NO 40
<211> LENGTH: 67
<212> TYPE: RNA
<213> ORGANISM: artificial sequence
<220> FEATURE:
<223> OTHER INFORMATION: synthetic construct

<400> SEQUENCE: 40
gcuauucuuu aagaagccug gcaauuaguu guuccuaua auugccaggc uucuaaagaa      60
auaacgc                                                               67

<210> SEQ ID NO 41
<211> LENGTH: 82
<212> TYPE: RNA
<213> ORGANISM: artificial sequence
<220> FEATURE:
<223> OTHER INFORMATION: synthetic construct

<400> SEQUENCE: 41
uuuaauguuc agcaggccuu uagaaaccua uaaguuaaua uaccauaucu auaaguuucu     60
gaaggccugc ugaguaccua aa                                              82

<210> SEQ ID NO 42
<211> LENGTH: 75
<212> TYPE: RNA
<213> ORGANISM: artificial sequence
<220> FEATURE:
<223> OTHER INFORMATION: synthetic construct

<400> SEQUENCE: 42
uaacccauau ggccucacua aagauaguua uauugaaaa acuacuaacu aucuuuagua     60
cggccauauu gguug                                                      75

<210> SEQ ID NO 43
<211> LENGTH: 80
<212> TYPE: RNA
<213> ORGANISM: artificial sequence
<220> FEATURE:
<223> OTHER INFORMATION: synthetic construct

<400> SEQUENCE: 43 caaaaggug aggguacagu gcuauauuau aguugaaac ucucacaauu uauaauaagc       60
acuguacccu caccuguuug                                                 80

<210> SEQ ID NO 44
<211> LENGTH: 1056
<212> TYPE: DNA
<213> ORGANISM: artificial sequence
```

```
<220> FEATURE:
<223> OTHER INFORMATION: synthetic construct

<400> SEQUENCE: 44
attagtcgac tggcctggat cataattgcc aatttccaag ccaaatatga tccaagccag      60
tctactaatc ccgaaacgac gaccagctaa ttgtgagcca cctaaggtcc cgatcctaag     120
agcattcgac gtctttcatg tttcaatctc acataaaagt cgtccaatgc tcttaagatc     180
ctggccacat cgtcgcaact tcaaatcaat taaatcaaaa aatcaagagt aagtgatatt     240
gggcactcca gttttaaaat tgaacgtgtg gagcggtaag taaatctttt tcaaagaaag     300
gtttcgatta agcgaagttt tacctaccag ctgcacaatt ataattttaa attcaacatg     360
ctcagtaaag ttgcgagtga aaattaaaat attatggagc ggttgcaatt agttctacgg     420
cacaaaagga ctcttatgat ttttccggtc attttgtccg tttctgccag agagttcgtt     480
gtggcattag cagcaccacg agtcaagaaa ttatgttaag tgatcccaa attcatcggg      540 ccattcgcta ttctttaaga agcctggcaa ttagttgttt cctataattg ccaggcttct     600
aaagaaataa cgcatgttta aagtccacaa ctcatcaagg aaaatgaaag tcaaagttgg     660
cagcttactt aaactaatc acagccttta atgttcagca ggcctttaga aacctataag      720
ttaatatacc atatctataa gtttctgaag gcctgctgag tacctaaagt gcctaacatc     780
attatttaat tttttttttt tttggcacac gaataaccat gccgtttta acccatatgg      840 cctcactaaa gatagttatt attgaaaaac tactaactat ctttagtacg gccatattgg     900
ttgcacggcc aattccaacg atttgtcatt tgtggcacgc atttgtgtca cctcagtgcg     960
aaaattgaaa attgtacaaa aaggtgaggg tacagtgcta tattatagtt tgaaactctc    1020
acaatttata ataagcactg taccctcacc tgtttg                               1056

<210> SEQ ID NO 45
<211> LENGTH: 1025
<212> TYPE: DNA
<213> ORGANISM: artificial sequence
<220> FEATURE:
<223> OTHER INFORMATION: synthetic construct

<400> SEQUENCE: 45
attagtcgac tggcctggat cataattgcc aatttccaag ccaaatatga tccaagccag      60
tctactaatc ccgaaacgac gaccagctaa ttgtgagcca cctaaggtcc cgatcctaag     120
agcattcgac gtctttcatg tttcaatctc acataaaagt cgtccaatgc tcttaagatc     180
ctggccacat cgtcgcaact tcaaatcaat taaatcaaaa aatcaagagt aagtgatatt     240
gggcactcca gttttaaaat tgaacgtgtg gagcggtaag taaatctttt tcaaagaaag     300
gtttcgatta agcgaagttt tacctaccag ctgcacaatt ataattttaa attcaacatg     360
ctcagtaaag ttgcgagtga aaattaaaat attatggagc ggttgcaatt agttctacgg     420
cacaaaagga ctcttatgat ttttccggtc attttgtccg tttctgccag agagttcgtt     480
gtggcattag cagcaccacg agtcaagaaa ttatgttaag tgatcccaa attcatcggg      540 ccattcgcta ttctttaaga agcctggcaa ttagttgttt cctataattg ccaggcttct     600
aaagaaataa cgcatgttta aagtccacaa ctcatcaagg aaaatgaaag tcaaagttgg     660
cagcttactt aaactaatc acagccttta atgttcagca ggcctttaga aacctataag      720
ttaatatacc atatctataa gtttctgaag gcctgctgag tacctaaagt gcctaacatc     780
attatttaat tttttttttt ttggcacacg aataaccatg ccgttttaa cccatatggc      840 ctcactaaag atagttatta ttgaaaaact actaactatc tttagtacgg ccatattggt     900
```
tgcacggcca attccaacga tttgtcattt gtggcacgca tttgtgtcac ctcagtgcga    960
aaattgaaaa ttgtacaaac aggtgagggt acagtgctta ttataaattg tgagagtttc   1020
aaact                                                                1025

<210> SEQ ID NO 46
<211> LENGTH: 1021
<212> TYPE: DNA
<213> ORGANISM: artificial sequence
<220> FEATURE:
<223> OTHER INFORMATION: synthetic construct

<400> SEQUENCE: 46
attagtcgac tggcctggat ctaattgcca attccaagcc aaatatgatc caagccagtc     60
tactaatccc gaaacgacga ccagctaatt gtgagccacc taaggtcccg atcctaagag    120
cattcgacgt ctttcatgtt tcaatctcac ataaaagtcg tccaatgctc ttaagatcct    180
ggccacatcg tcgcaacttc aaatcaatta atcaaaaaa tcaagagtaa gtgatattgg     240
gcactccagt tttaaaattg aacgtgtgga gcggtaagta aatcttttc aaagaaaggt    300 ttcgattaag cgaagtttta cctaccagct gcacaattat aattttaaat tcaacatgct    360
cagtaaagtt gcgagtgaaa attaaaatat tatggagcgg ttgcaattag ttctacggca    420
caaaaggact cttatgattt ttccggtcat tttgtccgtt tctgccagag agttcgttgt    480
ggcattagca gcaccacgag tcaagaaatt atgttaagtg atccccaaat tcatcgggcc    540
attcgctatt ctttaagaag cctggcaatt agttgtttcc tataattcca ggcttctaaa    600 gaataacgc atgtttaaag tccacaactc atcaaggaaa atgaaagtca agttggcag     660 cttacttaaa cttaatcaca gcctttaatg ttcagcaggc ctttagaaac ctataagtta    720 ataccata tctataagtt tctgaaggcc tgctgagtac ctaaagtgcc taacatcatt      780 atttaattt tttttttttt ggcacacgaa taaccatgcc gttttaacc catatggcct      840 cactaaagat agttattatt gaaaaactac taactatctt tagtacgacc atattggttg    900
cacggccaat ccaacgatt tgtcatttgt ggcacgcatt tgtgtcacct cagtgcgaaa    960
attgaaaatt gtacaaaaag gtgagggtac agtgctatat tatagtttga aactctcaaa   1020
t                                                                   1021

<210> SEQ ID NO 47
<211> LENGTH: 23
<212> TYPE: RNA
<213> ORGANISM: Heterodera glycines

<400> SEQUENCE: 47
uaauacuguc agguaaagau guc 23

<210> SEQ ID NO 48
<211> LENGTH: 25
<212> TYPE: RNA
<213> ORGANISM: Heterodera glycines

<400> SEQUENCE: 48
ugaaagacau ggguaguaug agacg 25

<210> SEQ ID NO 49
<211> LENGTH: 24
<212> TYPE: RNA
<213> ORGANISM: Heterodera glycines

<400> SEQUENCE: 49

-continued uaagugaauu cuuugccaca gucu                                          24

<210> SEQ ID NO 50
<211> LENGTH: 22
<212> TYPE: RNA
<213> ORGANISM: Heterodera glycines

<400> SEQUENCE: 50
aacccguaga uccgaacuag uc                                            22

<210> SEQ ID NO 51
<211> LENGTH: 23
<212> TYPE: RNA
<213> ORGANISM: Heterodera glycines

<400> SEQUENCE: 51
aacccguaga uccgaacuag ucu                                           23

<210> SEQ ID NO 52
<211> LENGTH: 22
<212> TYPE: RNA
<213> ORGANISM: Heterodera glycines

<400> SEQUENCE: 52
aacccguaga uccgaacuug ug                                            22

<210> SEQ ID NO 53
<211> LENGTH: 21
<212> TYPE: RNA
<213> ORGANISM: Heterodera glycines

<400> SEQUENCE: 53
gucagccgau ccuaaggcac c                                             21

<210> SEQ ID NO 54
<211> LENGTH: 22
<212> TYPE: RNA
<213> ORGANISM: Heterodera glycines

<400> SEQUENCE: 54
uggugcgugg acuaguggug ag                                            22

<210> SEQ ID NO 55
<211> LENGTH: 25
<212> TYPE: RNA
<213> ORGANISM: Heterodera glycines

<400> SEQUENCE: 55
ugaaagacau ggguaguaug agacg                                         25

<210> SEQ ID NO 56
<211> LENGTH: 23
<212> TYPE: RNA
<213> ORGANISM: Heterodera glycines

<400> SEQUENCE: 56
caccuauacu ccaccgucau ugg                                           23

<210> SEQ ID NO 57
<211> LENGTH: 90
<212> TYPE: RNA
<213> ORGANISM: Heterodera glycines

<400> SEQUENCE: 57

```
ucuuggaguc gggugguuug ggaucgcagc ccaaaucagg ugguaaacuu ugaauguggg    60
ucagccgauc cuaaggcacc ggcuaacgcc                                    90

<210> SEQ ID NO 58
<211> LENGTH: 75
<212> TYPE: RNA
<213> ORGANISM: Heterodera glycines

<400> SEQUENCE: 58
acaggcggcu uuugcccgug gcugcgugcu guucuuucgg ggauggugcg uggacuagug    60
gugagagcug cuugu                                                    75

<210> SEQ ID NO 59
<211> LENGTH: 75
<212> TYPE: RNA
<213> ORGANISM: Heterodera glycines

<400> SEQUENCE: 59
acaggcggcu uuugcccgug gcugugugcu guucuuucgg ggauggugcg uggacuagug    60
gugagagcug cuugu                                                    75

<210> SEQ ID NO 60
<211> LENGTH: 75
<212> TYPE: RNA
<213> ORGANISM: Heterodera glycines

<400> SEQUENCE: 60
acaggcggcu uuugcccgug gcugcgugcu guucuuucgg ggauggugcg uggacuagug    60
gugagagcuc ccucc                                                    75

<210> SEQ ID NO 61
<211> LENGTH: 75
<212> TYPE: RNA
<213> ORGANISM: Heterodera glycines

<400> SEQUENCE: 61
acagacggcu uuugcccgug gcugcgugcu guucuuucgg ggauggugcg uggacuagug    60
gugagagcug cuugu                                                    75

<210> SEQ ID NO 62
<211> LENGTH: 75
<212> TYPE: RNA
<213> ORGANISM: Heterodera glycines

<400> SEQUENCE: 62
acaggcggcu uuugcccgug gcugcuugcu guuccuucgg ggauggugcg uggacuagug    60
gugagagcug cuugu                                                    75

<210> SEQ ID NO 63
<211> LENGTH: 75
<212> TYPE: RNA
<213> ORGANISM: Heterodera glycines

<400> SEQUENCE: 63
acaggcggcu uuucuccgug gcugcuugcu guuccuucgg ggauggugcg uggacuagug    60
gugagagcug cuugu                                                    75

<210> SEQ ID NO 64
<211> LENGTH: 75
```

```
<212> TYPE: RNA
<213> ORGANISM: Heterodera glycines

<400> SEQUENCE: 64
acaggcggcu uuugcccgug gcugcuugcu guuccuucgg ggauggugcg uggacuagug    60
gugagagcug cucaa                                                    75

<210> SEQ ID NO 65
<211> LENGTH: 92
<212> TYPE: RNA
<213> ORGANISM: Heterodera glycines

<400> SEQUENCE: 65
gaccagaugc ugaaagacau ggguaguaug agacguucgu guguguaaau gccaaaaguc    60
gugucaucua cucuguuuuu cggcauuugc cu                                 92

<210> SEQ ID NO 66
<211> LENGTH: 98
<212> TYPE: RNA
<213> ORGANISM: Heterodera glycines

<400> SEQUENCE: 66
ucaacgcaac caccacgacc cuccuacacg ucauggccag acuacgcgac aagcacgugu    60
acaagccaau gacgguggag uauagguggc ccgcucca                           98

<210> SEQ ID NO 67
<211> LENGTH: 98
<212> TYPE: RNA
<213> ORGANISM: Heterodera glycines

<400> SEQUENCE: 67
ucaacgcaac cacuacgacc cuccuacacg ucauggccag acuacgcgac aagcacgugu    60
acaagccaau gacgguggag uauagguggc ccgcucca                           98

<210> SEQ ID NO 68
<211> LENGTH: 97
<212> TYPE: RNA
<213> ORGANISM: Heterodera glycines

<400> SEQUENCE: 68
caacgcaacc accacgaccc uccuacacgu cauggccaga cuacgcgaca agcacgugua    60
caagccaaug acgguggagu auaguggcc cgcucca                             97

<210> SEQ ID NO 69
<211> LENGTH: 98
<212> TYPE: RNA
<213> ORGANISM: Heterodera glycines

<400> SEQUENCE: 69
uggagcgggc caccuauacu ccaccgucau uggcuguac acgcuugu cgcguagucu       60 ggccaugacg uguaugaggg ucguggugu ugcguuga                            98

<210> SEQ ID NO 70
<211> LENGTH: 24
<212> TYPE: DNA
<213> ORGANISM: Diabrotica virgifera

<400> SEQUENCE: 70
tggaagacta gtgattttgt tgtt                                          24
```

```
<210> SEQ ID NO 71
<211> LENGTH: 23
<212> TYPE: DNA
<213> ORGANISM: Diabrotica virgifera

<400> SEQUENCE: 71
tctttggtta tctagctgta tga                                              23

<210> SEQ ID NO 72
<211> LENGTH: 21
<212> TYPE: DNA
<213> ORGANISM: Diabrotica virgifera

<400> SEQUENCE: 72
tcagtctttt tctctctcct a                                                21

<210> SEQ ID NO 73
<211> LENGTH: 21
<212> TYPE: DNA
<213> ORGANISM: Diabrotica virgifera

<400> SEQUENCE: 73
ggcaagatgt cggcatagct g                                                21

<210> SEQ ID NO 74
<211> LENGTH: 22
<212> TYPE: DNA
<213> ORGANISM: Diabrotica virgifera

<400> SEQUENCE: 74
tgaaagacat gggtagtgag at                                               22

<210> SEQ ID NO 75
<211> LENGTH: 22
<212> TYPE: DNA
<213> ORGANISM: Diabrotica virgifera

<400> SEQUENCE: 75
aattgcactt gtcccggcct gc                                               22

<210> SEQ ID NO 76
<211> LENGTH: 22
<212> TYPE: DNA
<213> ORGANISM: Diabrotica virgifera

<400> SEQUENCE: 76
tcaggtacct gaagtagcgc gc                                               22

<210> SEQ ID NO 77
<211> LENGTH: 22
<212> TYPE: DNA
<213> ORGANISM: Diabrotica virgifera

<400> SEQUENCE: 77
tgactagatc cacactcatt aa                                               22

<210> SEQ ID NO 78
<211> LENGTH: 22
<212> TYPE: DNA
<213> ORGANISM: Diabrotica virgifera

<400> SEQUENCE: 78
attgtacttc atcaggtgct ct                                               22
```

```
<210> SEQ ID NO 79
<211> LENGTH: 108
<212> TYPE: DNA
<213> ORGANISM: Drosophila melanogaster

<400> SEQUENCE: 79
gtcctcctgg gagtgcattc cgtatggaag actagtgatt tgttgtttg gtctttggta    60 ataacaataa atcccttgtc ttcttacggc gtgcatttgt gctcttca               108

<210> SEQ ID NO 80
<211> LENGTH: 98
<212> TYPE: DNA
<213> ORGANISM: Drosophila melanogaster

<400> SEQUENCE: 80
tatacagggt gctatgttgt ctttggttat ctagctgtat gagtgataaa taacgtcata    60
aagctagctt accgaagtta atattagcgt ctgcccag                           98

<210> SEQ ID NO 81
<211> LENGTH: 83
<212> TYPE: DNA
<213> ORGANISM: Drosophila melanogaster

<400> SEQUENCE: 81
ctgcaaccta tgtgggagcg agacggggac tcactgtgct tattaaatag tcagtctttt    60
tctctctcct atacaaattg cgg                                            83

<210> SEQ ID NO 82
<211> LENGTH: 112
<212> TYPE: DNA
<213> ORGANISM: Drosophila melanogaster

<400> SEQUENCE: 82
cgctgactgt tccattgaac aactgactag atgcagcata gcgctcttca aaatcgcttt    60
tcaacgtcag ctatgccgac atcttgccaa tttaccaacg gagttgatat ac           112

<210> SEQ ID NO 83
<211> LENGTH: 114
<212> TYPE: DNA
<213> ORGANISM: Drosophila melanogaster

<400> SEQUENCE: 83
cacagaggtt gtctgctctg aacgatgaaa gacatgggta gtgagacgtc ggagcctcgt    60
cgtatcacta ttctgttttt cgccgtcggg atcgtgacct ggaagctgta aact         114

<210> SEQ ID NO 84
<211> LENGTH: 115
<212> TYPE: DNA
<213> ORGANISM: Drosophila melanogaster

<400> SEQUENCE: 84
gccgaatata aatatgaatt tcccgtagga cgggaaggtg tcaacgtttt gcatttcgaa    60
taaacattgc acttgtcccg gcctatgggc ggtttgtaat aaacaactaa aatct        115

<210> SEQ ID NO 85
<211> LENGTH: 118
<212> TYPE: DNA
<213> ORGANISM: Drosophila melanogaster

<400> SEQUENCE: 85
ttcccccgac tgtaaagtct cctaccttgc gcgctaatca gtgaccgggg ctggtttttt    60
```

```
atatacagtc aggtacctga agtagcgcgc gtggtggcag acatatatct ccatcttc        118
```

```
<210> SEQ ID NO 86
<211> LENGTH: 120
<212> TYPE: DNA
<213> ORGANISM: Drosophila melanogaster

<400> SEQUENCE: 86
agctggaatt ggaattcata ctactgtttt tagtgggtgg gggtccagtg tttcacattg        60
attttcttag tatttgtgac tagatccaca ctcattaata acggtagttc aatcatcaag       120
```

```
<210> SEQ ID NO 87
<211> LENGTH: 93
<212> TYPE: DNA
<213> ORGANISM: Drosophila melanogaster

<400> SEQUENCE: 87
aactgtctcc catgtctatt gtacttcatc aggtgctctg gtgtgtctcg taacccggca        60
catgttgaag tacactcaat atgaggcgat ttg                                    93
```

```
<210> SEQ ID NO 88
<211> LENGTH: 951
<212> TYPE: DNA
<213> ORGANISM: artificial sequence
<220> FEATURE:
<223> OTHER INFORMATION: synthetic construct

<400> SEQUENCE: 88
gtcctcctgg gagtgcattc cgtatggaag actagtgatt tgttgtttg gtctttggta        60 ataacaataa atcccttgtc ttcttacggc gtgcatttgt gctcttcata tacagggtgc       120
tatgttgtct ttggttatct agctgtatga gtgataaata acgtcataaa gctagcttac       180
cgaagttaat attagcgtct gcccagctgc aacctatgtg ggagcgagac ggggactcac       240
tgtgcttatt aaatagtcag tcttttttctc tctcctatac aaattgcggc gctgactgtt      300
ccattgaaca actgactaga tgcagcatag cgctcttcaa aatcgctttt caacgtcagc       360
tatgccgaca tcttgccaat ttaccaacgg agttgatata ccacagaggt tgtctgctct       420
gaacgatgaa agacatgggt agtgagacgt cggagcctcg tcgtatcact attctgtttt       480
tcgccgtcgg gatcgtgacc tggaagctgt aaactgccga atataaatat gaatttcccg       540
taggacggga aggtgtcaac gttttgcatt tcgaataaac attgcacttg tcccggccta       600
tgggcggttt gtaataaaca actaaaatct ttccccgac tgtaaagtct cctaccttgc        660
gcgctaatca gtgaccgggg ctggttttt atatacagtc aggtacctga agtagcgcgc       720
gtggtggcag acatatatct ccatcttcag ctggaattgg aattcatact actgttttta      780
gtgggtgggg gtccagtgtt tcacattgat tttcttagta tttgtgacta gatccacact      840
cattaataac ggtagttcaa tcatcaagaa ctgtctccca tgtctattgt acttcatcag      900
gtgctctggt gtgtctcgta acccggcaca tgttgaagta cactcaatat g               951
```

```
<210> SEQ ID NO 89
<211> LENGTH: 21
<212> TYPE: DNA
<213> ORGANISM: Heterodera glycines

<400> SEQUENCE: 89
tcttgagact gtcctgtatt a                                                 21
```

-continued

```
<210> SEQ ID NO 90
<211> LENGTH: 515
<212> TYPE: DNA
<213> ORGANISM: Heterodera glycines

<400> SEQUENCE: 90
ccaccccgtg agattcacct caactcgcca ttcaacatcc ggaccatcta caacttccgc      60
ctgatcaaca cgggctcaaa gcgcattggg ttcgccttca agacgacgaa gccgaagcgc     120
atcttcctga acccgccgtg cggcaccgtg ggcgtcggcg acaccgtgaa cgtgatcatc     180
accgtggcac ccttcgaccc gaacaacgag gacatcaaga cgatcgcgt gatcgtggaa      240 tggtgcaacg cgcccggccc gtctgacgcc gtgttcaact ggactggtt caccgaaaat     300 gcggttcgaa atgtgcgcct caacgtcgtc tacaacttgt agcggatgca atatgatgat     360
ctgtatcgat ccatttcatg aaatgtattt caatgatcac tgttatcttg agactgtcct     420
gtattatgtg ttccgttttt tcatcatcat gaaatgtatt tcaatgatca cggaacgata     480
aatcggcgct agtgtaaaaa aaaaaaaaaa aaaaa                                515

<210> SEQ ID NO 91
<211> LENGTH: 21
<212> TYPE: RNA
<213> ORGANISM: artificial sequence
<220> FEATURE:
<223> OTHER INFORMATION: synthetic construct

<400> SEQUENCE: 91
uaauacagga cagucucaag a                                                21

<210> SEQ ID NO 92
<211> LENGTH: 90
<212> TYPE: RNA
<213> ORGANISM: artificial sequence
<220> FEATURE:
<223> OTHER INFORMATION: synthetic construct

<400> SEQUENCE: 92
ucuuggaguc ucugugggau uguccgucua ccaaaucagg ugguaaacuu ugaauguggu      60
aauacaggac agucucaaga ggcuaacgcc                                       90

<210> SEQ ID NO 93
<211> LENGTH: 22
<212> TYPE: DNA
<213> ORGANISM: Heterodera glyciness

<400> SEQUENCE: 93
tggtgcgtgg actagtggtg ag                                               22

<210> SEQ ID NO 94
<211> LENGTH: 1807
<212> TYPE: DNA
<213> ORGANISM: Heterodera glyciness

<400> SEQUENCE: 94
gcacgaggtc tatttgtttt ttattcaatt tcgacctgaa tgtcagctgc ggtttcttct      60
tcgcgtccga tggaagattg gaaatctgag ttagctatgc cagacaagga ccttcgatac    120
aaaacatctg atgtgactgc gactaagggc gttgaatttg aggaatttgg gctcactcgc    180
gaccttctta aaggcatttt tgagaagggt tgggagcatc caagtccggt tcaggaagcg    240
tcgattggaa ttgcacttac aggccaagac attctcgctc gcgccaaaaa tggaactggc    300
aaaactggcg catattgcat tccctgcatt gagaaaattg acccatcaaa agaatacatc    360
```

```
caagcaatga taatcgttcc aactcgggag cttgccttac aaacatctca gatttgcgta    420
gaactcagca aacacttgaa gattaagatt atggtgacga ctggcggaac agatcttcgt    480
gacgatattt tgcgtctcaa tggtattgta catcttgttg tggcaactcc tggccgaatt    540
ttggatctta tggagaaggg agttgcgaat gttgcgtatt gcaagacgat cgttctcgat    600
gaagcggaca aactcctttc ccaggacttc caaggtgtgc ttgaccgtct tgttcagttt    660
ctacccaaag accgtcaaat tatgctgtac tccgcaacat ttccgcgcac tgtcgcgact    720
tttatgaaaa agcacatgag caagccgtat gaaatcaatc tgatggagga actgacgctg    780
cttggcatta cacagtttta tgcttatgtc caagaaaaac agaaagtgca ctgtctgaac    840
acgcttttcc gcaagctcca aataaaccaa tccatcatct tttgtaattc gacacaacgg    900
gtggagttac ttgccaagaa aatcacagaa ttgggctact cctgttacta cattcattcc    960
aaaatggctc aacaccacag gaacagagtg ttccatgaat ttcgtcaggg tcattgtagg   1020
aacttggtct gttccgatct gcttactcgt ggtattgaca tccaagccgt caacgtggtc   1080
attaactttg acttcccgcg caattccgag acatatttgc acagaattgg acgttctggc   1140
cgttttggcc ccttggtatt gctatcaatc tgatcacctt tgaagaccgt tacaacctgc   1200
gacgcatcga aaggagctc aagacacaca ttgacccaat tccaaaggaa gtcgatccga   1260
aactctatgt tgctgaattt caaatggatc acaccaaatt cgactgtggg aatgtcgtcg   1320
atggtgcggt gctgaacaac ggagtcgacc aacaacagca gcctcgggct tcgtcgtagt   1380
tgcggtggga gcacggagcg aaaactccca cagaatttat cagctcgtcc atccacagta   1440
aattgaccct aataaaaatg ctgcgctgct ctccgatctc tcatttgttg ttaattttcg   1500
gattttgtta tttaaattct ctcatccgca cacgtccgtc acaccattca aatttatcgt   1560
ccattcattg tgcgaatttg gtatttctct gcgaacacat tgtgtggatt tctatctttg   1620
tgacctttta ataaatgtga gagggttttg tctttgttcg ttctcatcat tcacctcttt   1680
ctctccctca cctaaccaat aatcctccaa tttactgctt gtctattaac tttgttacgg   1740
gtaaattcca actatgcctc aaaaaaaaaa aaacaaaaaa aaaaaaaaa aaaaaaaaa     1800 aaaaaaa                                                            1807
```

<210> SEQ ID NO 95
<211> LENGTH: 22
<212> TYPE: RNA
<213> ORGANISM: artificial sequence
<220> FEATURE:
<223> OTHER INFORMATION: synthetic construct

<400> SEQUENCE: 95

```
uaaaagguca caaagauaga aa                                              22
```

<210> SEQ ID NO 96
<211> LENGTH: 85
<212> TYPE: RNA
<213> ORGANISM: artificial sequence
<220> FEATURE:
<223> OTHER INFORMATION: synthetic construct

<400> SEQUENCE: 96

```
acaggcggcu uuuuacguu uuggccuuuu guucuuucgg ggauaaaagg ucacaaagau     60
agaaaagcug cuuguagcug cuugu                                          85
```